US009623041B2

(12) United States Patent
Inoue et al.

(10) Patent No.: US 9,623,041 B2
(45) Date of Patent: Apr. 18, 2017

(54) POLYMALIC ACID-BASED NANOBIOPOLYMER COMPOSITIONS

(71) Applicant: Cedars-Sinai Medical Center, Los Angeles, CA (US)

(72) Inventors: Satoshi Inoue, Beverly Hills, CA (US); Hui Ding, Los Angeles, CA (US); Eggehard Holler, Los Angeles, CA (US); Keith L. Black, Los Angeles, CA (US); Julia Y. Ljubimova, Studio City, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 114 days.

(21) Appl. No.: 13/930,533

(22) Filed: Jun. 28, 2013

(65) Prior Publication Data

US 2014/0193398 A1  Jul. 10, 2014

Related U.S. Application Data

(63) Continuation-in-part of application No. PCT/US2010/062515, filed on Dec. 30, 2010.

(51) Int. Cl.
*A61K 31/713* (2006.01)
*C07K 16/28* (2006.01)
*C07K 16/32* (2006.01)
*A61K 39/00* (2006.01)

(52) U.S. Cl.
CPC ........ *A61K 31/713* (2013.01); *C07K 16/2881* (2013.01); *C07K 16/32* (2013.01); *A61K 2039/505* (2013.01)

(58) Field of Classification Search
CPC ............... A61K 47/48; A61K 31/713; A61K 2039/505; A61K 39/39558; C07K 16/32
See application file for complete search history.

(56) References Cited

U.S. PATENT DOCUMENTS

| 7,332,585 | B2 | 2/2008 | Adams et al. |
| 7,618,626 | B2 | 11/2009 | Gualberto et al. |
| 2007/0259008 | A1 | 11/2007 | Ljubimova et al. |

FOREIGN PATENT DOCUMENTS

| KR | 10-2007-0036130 | | 4/2007 | |
| WO | WO 99/09045 | * | 2/1999 | ............. C07H 21/00 |
| WO | 2005055980 A2 | | 6/2005 | |
| WO | 2009/126913 | | 10/2009 | |

OTHER PUBLICATIONS

Bayse et al. (Nucleic Acids Research, 29: 4873-4880, 2001).*
Wiseman et al. (Cancer, 103(9): 1770-1777, 2005).*
Iversen et al. (Clinical Cancer Research, 9: 2510-2519, 2003).*
NCBI GenBank Accession No. NM_005228 (Dec. 26, 2010)—See the whole document.
NCBI GenBank Accession No. X03363 (Mar. 30, 1995)—See the whole document.
NCBI GenBank Accession No. X91171 (Oct. 7, 2008)—See the whole document.
NCBI GenBank Accession No. NM_002291 (Nov. 21, 2010)—See the whole document.
Ding, Hui et al. "Inhibition of brain tumor growth by intravenous poly(beta-L-malic acid) nanobioconjugate with pH-dependent drug release", Proceedings of the National Academy of Sciences, <Correction> vol. 107, No. 45, p. 19603 (Nov. 9, 2010).
Ding, Hui et al. "Inhibition of brain tumor growth by intravenous poly(beta-L-malic acid) nanobioconjugate with pH-dependent drug release", Proceedings of the National Academy of Sciences, vol. 107, No. 42, pp. 18143-18148 (Oct. 19, 2010).
Fujita, Manabu et al. "Overexpression of β1-chain-containing laminins in capillary basement membranes of human breast cancer and its metastases", Breast Cancer Research, vol. 7, No. 4, p. R411-R421 (Apr. 6, 2005) Retrieved from the Internet: <URL:http://breast-cancer-research.com/content/7/4/R411>.
Fujita, Manabu et al. "Inhibition of laminin-8 in vivo using a novel poly(malic acid)-based carrier reduces glioma angiogenesis", Angiogenesis, vol. 9, No. 4, pp. 183-191 (2006).
Inoue, Satoshi et al. "Newly designed nanobioconjugate for direct targeting and systemic treatment of HER2-positive breast cancer", Proceedings of the American Association for Cancer Research Annual Meeting, 101st Annual Meeting of the American Association for Cancer Research, Washington, D.C., vol. 51, p. 937 (Apr. 17-21, 2010).
Ljubimova, Julia Y. et al. "Nanoconjugate based on polymalic acid for tumor targeting", Chemico-Biological Interactions, vol. 171, pp. 195-203 (2008).
Ljubimova, Julia Y. et al. "Poly(malic acid) nanoconjugates containing various antibodies and oligonucleotides for multitargeting drug delivery", Nanomedicine, vol. 3(2), pp. 247-265 (Apr. 2008).
Office Action from corresponding European Patent Application No. 10 861 515.4 dated Feb. 26, 2014, 6 pages.
Office Action from corresponding Japanese Patent Application No. 2013-547442 dated Oct. 29, 2014, with a Brief Report in English, 6 pages.

* cited by examiner

*Primary Examiner* — Brad Duffy
*Assistant Examiner* — Nelson B Moseley, II
(74) *Attorney, Agent, or Firm* — Wilson Sonsini Goodrich & Rosati

(57) ABSTRACT

Nanobiopolymeric conjugates based on biodegradable, non-toxic and non-immunogenic poly (β-L-malic acid) PMLA covalently linked to molecular modules that include morpholino antisense oligonucleotides (AONa), an siRNA or an antibody specific for an oncogenic protein in a cancer cell, and an antibody specific for a transferrin receptor protein, are provided. Methods for treating a cancer in subject with nanobiopolymeric conjugates are described.

15 Claims, 8 Drawing Sheets

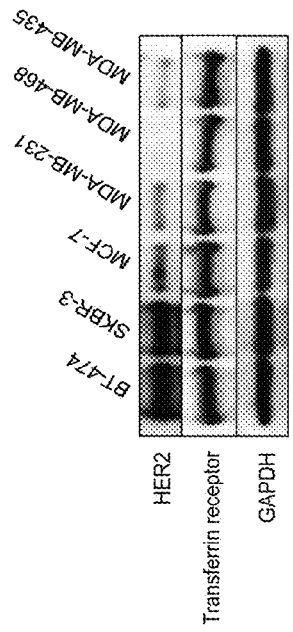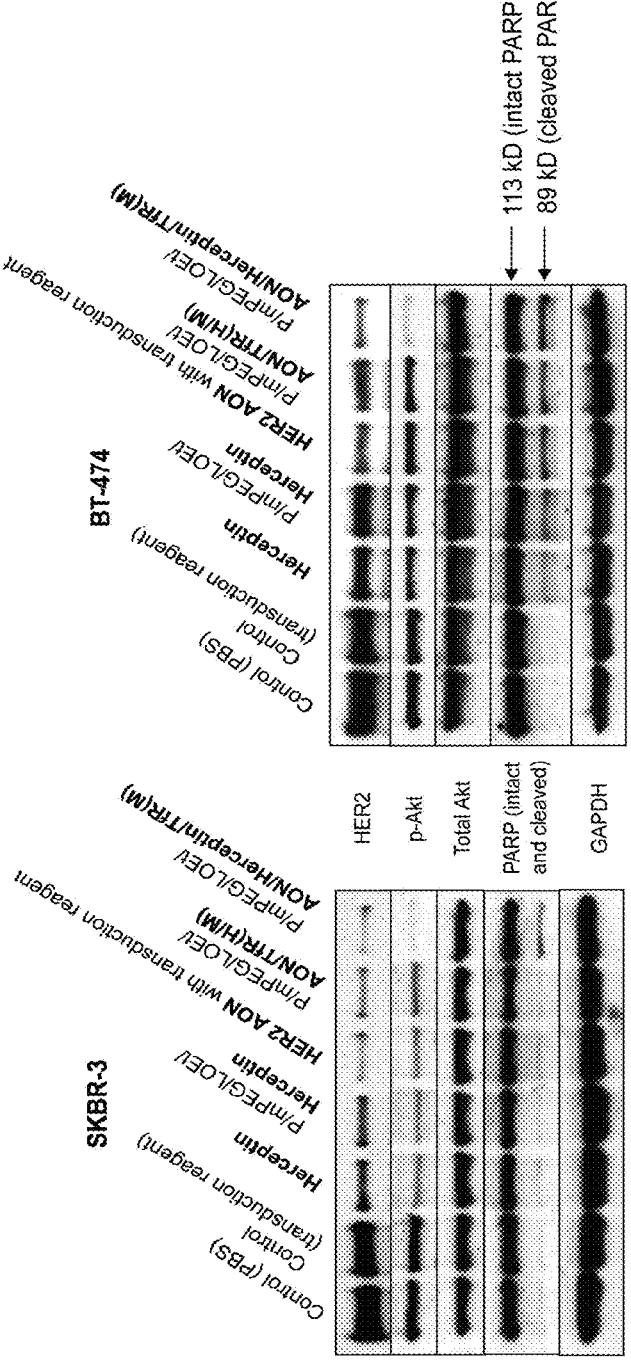
Figure 3A
Figure 3B
Figure 3C

SEQUENCE LISTING

```
<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: The sequence was designed and synthesized

<400> SEQUENCE: 1
agggagccgc agcttcatgt ctgtg                                           25

<210> SEQ ID NO 2
<211> LENGTH: 24
<212> TYPE: DNA
<213> ORGANISM: Artificial Sequence
<220> FEATURE:
<223> OTHER INFORMATION: The sequence was designed and synthesized
```

```
<400> SEQUENCE: 2
catggtgctc actgcggctc cggc                                          24

<210> SEQ ID NO 3
<211> LENGTH: 25
<212> TYPE: DNA
<213> ORGANISM: Artificial Sequence
<220> FEATURE:
<223> OTHER INFORMATION: The sequence was designed and synthesized

<400> SEQUENCE: 3
tcgctccggc tctcccgatc aatac                                         25

<210> SEQ ID NO 4
<211> LENGTH: 25
<212> TYPE: DNA
<213> ORGANISM: Artificial Sequence
<220> FEATURE:
<223> OTHER INFORMATION: The sequence was designed and synthesized

<400> SEQUENCE: 4
agctcaaagc catttctccg ctgac                                         25

<210> SEQ ID NO 5
<211> LENGTH: 25
<212> TYPE: DNA
<213> ORGANISM: Artificial Sequence
<220> FEATURE:
<223> OTHER INFORMATION: The sequence was designed and sythesized

<400> SEQUENCE: 5
ctagcaactg gagaagcccc atgcc                                         25

<210> SEQ ID NO 6
<211> LENGTH: 21
<212> TYPE: DNA
<213> ORGANISM: Artificial Sequence
<220> FEATURE:
<223> OTHER INFORMATION: The sequence is combination of DNA and RNA

<400> SEQUENCE: 6
ccuauaaugc uacgaauaut t                                             21

<210> SEQ ID NO 7
<211> LENGTH: 21
<212> TYPE: RNA
<213> ORGANISM: Artificial Sequence
<220> FEATURE:
<223> OTHER INFORMATION: The sequence was designed and synthesized

<400> SEQUENCE: 7
auauucguag cauuuaugga g                                             21

<210> SEQ ID NO 8
<211> LENGTH: 21
<212> TYPE: DNA
<213> ORGANISM: Artificial Sequence
<220> FEATURE:
<223> OTHER INFORMATION: The sequence is combination of DNA and RNA

<400> SEQUENCE: 8
guuggaugau ugacucugat t                                             21
```

```
<210> SEQ ID NO 9
<211> LENGTH: 21
<212> TYPE: DNA
<213> ORGANISM: Artificial Sequence
<220> FEATURE:
<223> OTHER INFORMATION: The sequence is combination of DNA and RNA

<400> SEQUENCE: 9
ucagagucaa ucauccaaca t                                                   21
```

POLYMALIC ACID-BASED NANOBIOPOLYMER COMPOSITIONS

CROSS REFERENCE TO RELATED APPLICATION

This application claims the benefit and is a continuation-in-part of PCT Patent Application Serial No. PCT/US2010/062515, filed Dec. 30, 2010, which is incorporated by reference as if fully set forth.

STATEMENT REGARDING FEDERALLY SPONSORED RESEARCH OR DEVELOPMENT

The invention was made with government support under Grant No. CA123495 and Grant No. CA136841 awarded by National Institutes of Health. The government has certain rights in the invention.

The sequence listing filed with this application, titled "Sequence Listing," having a file size of 2,285 bytes, and created Jun. 30, 2013 is incorporated herein by reference as if fully set forth.

The Substitute Sequence Listing filed on Sep. 17, 2013, having a file size of 2,300 bytes, and created Sep. 17, 2013, is incorporated herein by reference as if fully set forth.

FIELD OF INVENTION

The present invention generally relates to compositions and methods for treating patients having cell proliferative disorders with polymalic acid-based nanobiopolymeric compositions that inhibit synthesis and activity of an oncogenic protein.

BACKGROUND

Breast cancer is a disease affecting a significant population of women around the world. About 1 in 8 women in the United States (between 12 and 13%) will develop invasive breast cancer over the course of her lifetime. Prognosis and survival rate varies greatly depending on cancer type and staging. Breast cancers expressing genetic characteristics such as human epidermal growth factor receptor-2 (HER2) are associated with a poor prognosis.

Research has focused on the use of recombinant humanized monoclonal antibodies for the treatment of cancers with cells that overexpress protein p185HER2. This 185-kDa growth factor receptor is encoded by the her-2 proto-oncogene, also referred to as neu and c-erbB-2 (Slamon et al. 1987 Science 235:177). The her-2 gene is closely related to the gene encoding epidermal growth factor receptor (EGFR). Amplification of the her-2 gene has been linked to neoplastic transformation in human breast cancer cells (Slamon et al. 1987 Science 235:177). Overexpression of the HER2 protein has been identified in 20-30% of breast cancer patients, and has been correlated with regionally advanced disease, increased probability of tumor recurrence, and reduced patient survival. As many as 30-40% of patients having gastric, endometrial, salivary gland, non-small cell lung, pancreatic, ovarian, peritoneal, prostate, or colorectal cancers may also exhibit overexpression of this protein.

A more difficult-to-treat form of HER2-negative breast cancer known as "triple-negative," affects some patients. This form tests negative for three primary receptors: HER2, estrogen receptor and progesterone receptor. However, it is positive for epidermal growth factor receptor (EGFR, HER1).

Humanized anti-HER2/neu monoclonal antibody trastuzumab (Herceptin®, Genentech Inc., San Francisco, Calif.) is used alone or combined with chemotherapy for treatment of patients with advanced breast cancer overexpressing HER2/neu (Baselga J. 2006 Science 312:1175; Baselga J et al. 1999 Semin Oncol 26:78; Slamon D J et al. 2009 J Natl Cancer Inst 101:615), with significant anti-tumor effect. However, serious adverse effects on normal organs have been reported (Keef D L. 2002 Cancer 95:1592; Vahid B et al, 2008 Chest 133:528). Moreover, many patients develop resistance to Herceptin® within one year of treatment, which renders this treatment ineffective (Tseng P H et al. 2006 Mol Pharmacol 70:1534). Therefore, new drugs with minimal side effects for non-tumor tissues are urgently needed to improve HER2/neu-positive tumor therapy.

SUMMARY

In an aspect, the invention relates to a drug delivery composition for treating a cancer in a subject. The drug delivery composition includes a plurality of biologically active molecular modules comprising at least one module that targets a tumorigenic cell or a cancer cell, at least one module that inhibits synthesis or activity of a human epidermal growth factor receptor (HER) protein in the cell, and at least one module for cytoplasmic delivery. The drug delivery composition also includes a polymalic acid-based molecular scaffold. The molecular modules are covalently linked to the scaffold.

In an aspect, the invention relates to a kit for treating a patient having a cancer. The kit includes a drug delivery composition comprising a nanobiopolymeric conjugate of a scaffold that includes a PMLA and molecular modules. The molecular modules includes an antisense molecule that substantially inhibits synthesis or activity of a HER protein, a molecular module to facilitate delivery of the antisense molecule to cytoplasm, at least one targeting antibody specific for the HER protein, at least one antibody specific for a tumor vasculature protein, and a molecular module that prolongs circulation of the composition. The PMLA is covalently linked to the molecular modules, in a container.

In an aspect, the invention relates to a method for treating a cancer in a subject. The method includes contacting the subject with a drug delivery composition. The drug delivery composition includes a PMLA covalently linked to a plurality of molecular modules. The molecular modules include at least one module that targets a tumorigenic cell or a cancer cell, at least one module that inhibits synthesis or activity of a HER protein in the cell, and at least one module for cytoplasmic delivery. The drug delivery composition is effective for inhibiting at least one of tumor growth, tumor regression and eliminating of cancer in a subject.

BRIEF DESCRIPTION OF THE DRAWINGS

The following detailed description of the preferred embodiments will be better understood when read in conjunction with the appended drawings. For the purpose of illustration, there are shown in the drawings embodiments which are presently preferred. It is understood, however, that the invention is not limited to the precise arrangements and instrumentalities shown. In the drawings:

FIGS. 3A-3C illustrate photographs of immunoblots showing changes observed in HER2/neu expression, Akt phosphorylation, and apoptosis resulting from various treatments of breast cancer cells in vitro. FIG. 3A illustrates a comparison of HER2/neu and TfR expression in various cell lines. FIG. 3B illustrates expression analysis of various markers in cell line SKBR-3. FIG. 3C illustrates expression of the markers in cell line BT-474. HER2/neu overexpressing breast cancer cells shown in FIG. 3A treated with various compounds.

FIG. 6A illustrates data of histopathological analysis of respective tumors from two representative animals for each group administered with different drugs. FIG. 6B illustrates extent of tumor growth inhibition in mice. FIG. 6C illustrates expression of select markers after treatment of HER2/neu positive tumors in vivo.

FIG. 8A illustrates treatment with PBS as a negative control. FIG. 8B illustrates treatment with P/mPEG/LOEt/AON/Herceptin®/TfR(M).

DETAILED DESCRIPTION OF THE PREFERRED EMBODIMENTS

Figure 1:
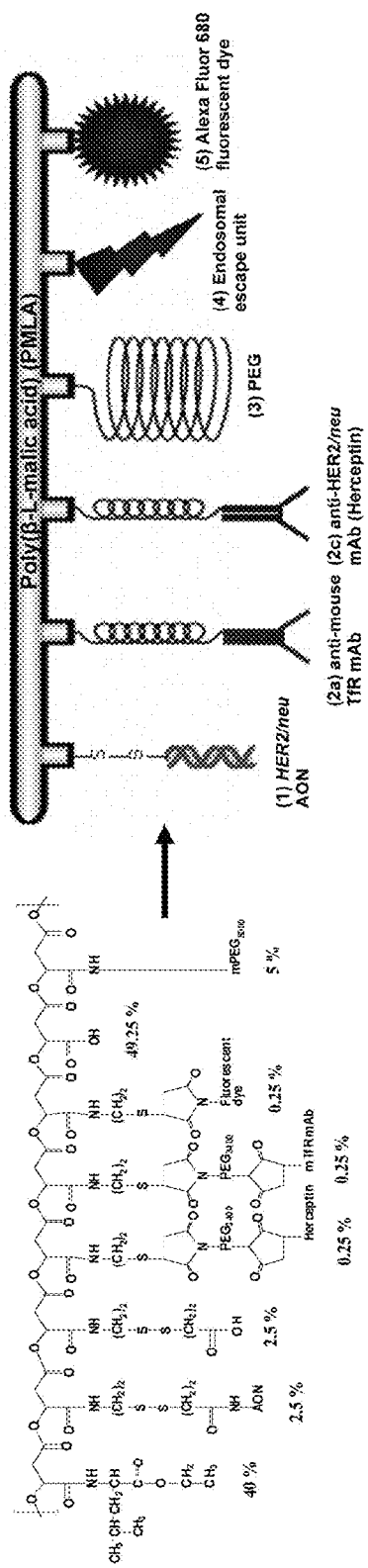
FIG. 1 illustrates a chemical structure and schematic drawings of a nanobiopolymeric conjugate designed to inhibit HER2/neu expression by antisense oligonucleotides (AON) and to attenuate HER2/neu-mediated cell signaling by Herceptin®.
Figure 1:
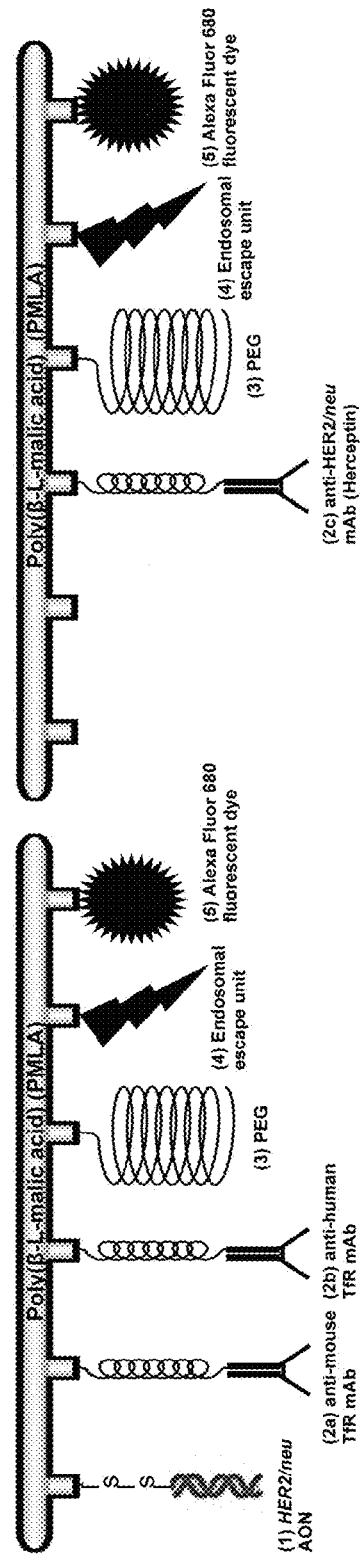

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

As used herein the term "molecular scaffold" refers to a molecule having at least two or more modules that transport a covalently conjugated drug to a targeted tissue; bind to cell surface receptors of the tissue; internalize into endosomes; escape the endosomes into the cytoplasm; and release reactive free drug in the cytoplasm by chemical reaction with glutathione and other sulfhydryl groups of the cytoplasmic content. The specificity of high molecular mass drug vehicles and particles rests primarily on the tumor tissue targeting by tumor-specific conjugated targeting molecules and their enhanced permeability and retention in tumors that originates from high molecular mass such as greater than 20000 (Duncan R. 1999 Research Focus 2:441; Seymour L W et al., 1995 Eur J Cancer Res 31A:766).

The term "polymalic acid" or PMLA as used herein refers to a polymer, e.g., a homopolymer that contains a main chain ester linkage, is biodegradable and of a high molecular flexibility, soluble in water (when ionized) and organic solvents (in its acid form), non-toxic, and non-immunogenic (Lee B et al., Water-soluble aliphatic polyesters: poly(malic acid)s, in: Biopolymers, vol. 3a (Doi Y, Steinbuchel A eds., pp 75-103, Wiley-VCH, New York 2002). Drug carrying PMLA is synthesized by ring-opening polymerization of derivatized malic acid lactones. Doxorubicin-poly-malic acid has been synthesized from synthetic poly-β-D, L-malic acid (Abdellaoui K et al., 1998 Eur J Pharmaceutical Sciences 6:61). The carrier consists of poly(β-L-malic acid), herein referred to as poly-β-L-malic acid or PMLA, representing the molecular backbone or scaffold that is chemically conjugated at its carboxylic groups at defined ratios with a variety of modules each of which performs at least one of the following functions: delivery of a pro-drug via a releasable functional module that becomes effective in the cytoplasm; directing the carrier towards a specific tissue by binding to the surfaces of cells, e.g., a monoclonal antibody (mAB); internalization into the targeted cell through endosomes (usually via internalization of a targeted surface receptor); promoting escape from endosomes into the cytoplasm by virtue of hydrophobic functional units that integrate into and finally disrupt endosomal membranes; increasing effectiveness during acidification of endosomes en route to lysosomes; and protection by polyethylene glycol (PEG) against degradative enzyme activities, e.g., peptidases, proteases, etc.

The term "module" as used herein refers to a biologically active molecular structure that forms a part of a composition herein, for example, a small drug molecule or a chromophore molecule; a protein molecule such as an antibody or lectin; or a portion thereof that are covalently joined to PMLA in constructing the composition. In the examples herein a biologically active module is exemplified by morpholino antisense oligonucleotides (AON) that are specific to HER2/neu receptor protein. Tissue targeting is exemplified by use of a monoclonal antibody (mAB) module that specifically recognizes and binds a transferrin receptor protein.

The term "transferrin receptor protein" as used herein refers to the receptor expressed on endothelium cell surfaces, and at elevated levels on certain tumors (Lee J H et al. 2001 Eur J Biochem 268:2004; Kovar M K et al., 2003 J Drug Targeting 10:23). Transferrin receptors are used as a target for a drug delivery system in compositions herein, to chemically bind to transferring, for example using a monoclonal antibody that binds the transferrin receptor and thereby achieves transcytosis through endothelium associated with blood brain barrier. Antibody binding to transferrin receptor and internalization into endosomes has been demonstrated (Broadwell R D et al., 1996 Exp Neurol 142:47). It will be appreciated that in the case of the transferrin receptor any appropriate antibody monoclonal antibody, for example, a humanized or chimeric antibody, or a lectin or another ligand specific to the transferrin receptor can be used. Other appropriate ligands to any number of cell surface receptors or antigens can be used as targets in the compositions herein and transferrin receptor is merely exemplary.

The phrase "endosomal escape unit" as used herein refers to a carrier module attached to the PMLA scaffold that becomes active by acidification during maturation of the endosomal vesicles towards lysosomes (Bulmus V et al., 2001 Cancer Research 61:5601; Lackey C A et al., 2002 Bioconjugate Chem 13:996). The carrier module includes a plurality of leucine or valine residues, or a leucine ethylester linked to the PMLA scaffold by amide bonds. During acidification of the endosomes en route to lysosomes, these stretches of the carrier molecule become charge-neutralized and hydrophobic, and capable of disrupting membranes. Other molecules that become charge neutralized at lysomal pH's may be used in place of leucine or valine residues, or a leucine ethylester in construction of the compositions containing PMLA and an endosomal escape unit module.

PEGylation is generally used in drug design to increase the in vivo half-life of conjugated proteins, to prolong the circulation time, and enhance extravasation into targeted solid tumors (Arpicco S et al. 2002 Bioconjugate Chem 13:757; Maruyama K et al., 1997 FEBS Letters 413:1771). Other molecules known to increase half-life may be used in design of compositions herein.

As used herein, the terms "cancer" and "cancerous" refer to the physiological condition in mammals in which a population of cells are characterized by unregulated cell growth. Examples of cancers include, without limitation, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

The terms "proliferative disorder" and "proliferative disease" refer to disorders associated with abnormal cell proliferation such as cancer.

The terms "tumor" and "neoplasm" as used herein refer to any mass of tissue that result from excessive cell growth or proliferation, either benign (noncancerous) or malignant (cancerous) including pre-cancerous lesions.

The term "primary cancer" refers to the original site at which a cancer originates. For example, a cancer originating in the breast is called a primary breast cancer. If it metastasizes, i.e., spreads to the brain, the cancer is referred to as a primary breast cancer metastatic to the brain.

The term "metastasis" as used herein refers to the process by which a cancer spreads or transfers from the site of origin to other regions of the body with the development of a similar cancerous lesion, i.e., having the same or substantially the same biochemical markers at the new location. A "metastatic" or "metastasizing" cell is one that has a reduced activity for adhesive contacts with neighboring cells and migrates by the bloodstream or within lymph from the primary site of disease to additional distal sites, for example, to invade neighboring body structures or distal structures.

The terms "cancer cell", "tumor cell" and grammatical equivalents refer to a cell derived from a tumor or a pre-cancerous lesion including both a non-tumorigenic cell and a tumorigenic cell, i.e., cancer stem cell.

As used herein "tumorigenic" refers to the functional features of a solid tumor stem cell including the properties of self-renewal i.e., giving rise to additional tumorigenic cancer cells, and proliferation to generate other tumor cells i.e., giving rise to differentiated and thus non-tumorigenic tumor cells, such that cancer cells form a tumor.

The phrase "target a tumorigenic cell or a cancer cell" as used herein refers to delivery of a composition to a population of tumor-forming cells within tumors, i.e., tumorigenic cells. The preferential delivery of the composition to the tumorigenic population of cancer cells in comparison to other populations of cells within tumors is referred herein as targeting to eliminate cancer cells, a property that improves specificity and efficacy of the composition.

The term "antibody" is used herein to mean an immunoglobulin molecule that is a functional module included in compositions herein for ability to recognize and specifically bind to a target, such as a protein, polypeptide, peptide, carbohydrate, polynucleotide, lipid, or combinations of the foregoing through at least one antigen recognition site within the variable region of the immunoglobulin molecule. In certain embodiments, antibodies included as functional modules of compositions herein include a class described as antagonist antibodies, which specifically bind to a cancer stem cell marker protein and interfere with, for example, ligand binding, receptor dimerization, expression of a cancer stem cell marker protein, and/or downstream signaling of a cancer stem cell marker protein. In alternative embodiments, antibodies as functional modules in compositions herein include agonist antibodies that specifically bind to a cancer stem cell marker protein and promote, for example, ligand binding, receptor dimerization, and/or signaling by a cancer stem cell marker protein. In alternative embodiments, antibodies that do not interfere with or promote the biological activity of a cancer stem cell marker protein instead function to inhibit tumor growth by, for example, antibody internalization and/or recognition by the immune system.

As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody includes any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. Antibodies can be naked or conjugated to other molecules such as toxins, radioisotopes, etc. In other embodiments an antibody is a fusion antibody.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

An "Fv antibody" refers to the minimal antibody fragment that contains a complete antigen-recognition and -binding site either as two-chains, in which one heavy and one light chain variable domain form a non-covalent dimer, or as a single-chain (scFv), in which one heavy and one light chain variable domain are covalently linked by a flexible peptide linker so that the two chains associate in a similar dimeric structure. In this configuration the complementarity determining regions (CDRs) of each variable domain interact to define the antigen-binding specificity of the Fv dimer. Alternatively a single variable domain (or half of an Fv) can be used to recognize and bind antigen, although generally with lower affinity.

A "monoclonal antibody" as used herein refers to homogenous antibody population involved in specific recognition and binding of a single antigenic determinant, or epitope. Polyclonal antibodies include a population of antibody species each directed to a different antigenic determinant. The term "monoclonal antibody" encompasses both and full-length monoclonal antibodies and antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to those obtained without limitation by methods including and not limited to hybridoma expression, phage selection, recombinant expression, and by transgenic animals.

In an embodiment, a drug delivery composition for treating a cancer in a subject is provided. The drug delivery composition may include a plurality of biologically active molecular modules. The plurality of the biologically active molecular modules may include at least one module that targets a tumorigenic cell or a cancer cell. The drug delivery composition may include at least one module that inhibits synthesis or activity of a human epidermal growth factor receptor (HER) protein in the cell. The drug delivery composition may include at least one module for cytoplasmic delivery. The drug delivery composition may include a polymalic acid-based molecular scaffold. The molecular modules may be covalently linked to the polymalic acid-based molecular scaffold. The HER protein may be at least one protein selected from the group consisting of: HER1, HER2, HER3 and HER4. The at least one module that inhibits synthesis or activity of the protein may be selected from the group consisting of: an antisense oligonucleotide (AON), an siRNA oligonucleotide, an antibody, a polypeptide, an oligopeptide and a low molecular weight drug. The scaffold in a related embodiment includes a poly-β-L-malic acid (PMLA). The PMLA may be also denoted as poly(-β-L-malic acid).

In an embodiment, the AON may be a Morpholino AON. The Morpholino AON may include a sequence complementary to a sequence contained in an mRNA transcript of HER2/neu protein. For example, the AON may be selected from: 5'-AGGGAGCCGCAGCTTCATGTCTGTG-3' (SEQ ID NO: 1), and 5'-CATGGTGCTCACTGCGGCTCCGGC-3' (SEQ ID NO:2).

In an embodiment, the at least one module that targets the cell may include an antibody that binds specifically to a vasculature protein in the cell. The vasculature protein may include a transferrin receptor protein. The antibody may be selected from at least one of: anti-human, rat anti-mouse, rat anti-human, rabbit anti-human and goat anti-human.

In an embodiment, the at least one module that inhibits activity of the protein includes an antibody binding specifically to a HER2/neu protein. The antibody may be Herceptin®.

In an embodiment, the drug delivery composition may include a Morpholino AON that include sequence complementary to a sequence contained in an mRNA transcript of an epidermal growth factor receptor (EGFR) or HER1 protein. The sequence of the Morpholino AON may include 5'-TCGCTCCGGCTCTCCCGATCAATAC-3' (SEQ ID NO:3).

In an embodiment, the drug delivery composition may include a Morpholino AON that includes a sequence complementary to a sequence contained in an mRNA transcript of at least one subunit of laminin-411. The subunit may be at least one of an α4 subunit and a β1 subunit. The sequence complimentary to the transcript of the α4 subunit may include the following sequence:
5'-AGCTCAAAGCCATTTCTCCGCTGAC-3' (SEQ ID NO:4). The sequence complimentary to the transcript of the β1 subunit may include the following sequence: 5'-CTAGCAACTGGAGAAGCCCCATGCC-3' (SEQ ID NO:5).

In an embodiment, the drug delivery composition may include the siRNA oligonucleotide. The siRNA oligonucleotide may include a sequence complementary to a gene encoding an EGFR/HER1 protein. The sequence may include a sense sequence as follows: 5'-CCUAUAAUGCUACGAAUAUtt-3' (SEQ ID NO:6). The sequence may include an antisense sequence as follows: 5'-AUAUUCGUAGCAUUUAUGGag-3' (SEQ ID NO:7).

In an embodiment, the siRNA oligonucleotide may include a sequence complementary to a gene encoding a HER2 protein. The sequence may include a sense sequence as follows: 5'-GUUGGAUGAUUGACUCUGAtt-3' (SEQ ID NO:8). The sequence may include an antisense sequence as follows: 5'-UCAGAGUCAAUCAUCCAACat-3' (SEQ ID NO:9).

In an embodiment, the at least one module for cytoplasmic delivery may include an endosome escape unit. The endosome escape unit may be but is not limited to leucine residues, valine residues, or a leucine ethylester. The endosome escape unit may be a plurality of leucine or valine residues, or a single or a plurality of leucine residues, or mixture of any of these. The leucine ethylester may be included in the drug delivery composition in a concentration of about 40% of the drug delivery composition.

In an embodiment, the plurality of modules of the drug delivery composition may further include a polyethylene glycol (PEG). The PEG may have a molecular weight of about 1,000 Da, about 5,000 Da, about 10,000 Da, about 15,000 Da, about 20,000 Da, about 25,000 Da, or about 30,000 Da.

In an embodiment, the drug delivery composition may be provided in a unit dose effective for treatment of the cancer in the patient. The unit dose may be at least one selected from: 1 μg/kg, 50 μg/kg, 100 μg/kg, 500 μg/kg, 1 mg/kg, 5 mg/kg, 10 mg/kg, 50 mg/kg, and 100 mg/kg. The unit dose may be at least 1 mg/kg. The unit dose may be less than about 10 mg/kg.

In an embodiment, the cancer is at least one selected from the list of: gastric, endometrial, salivary gland, lung, non-small cell lung, pancreatic, ovarian, peritoneal, prostate, colorectal, breast, cervical, uterine, ovarian, brain, head and neck, testicular and teratoma cancers. The breast cancer may be a triple-negative breast cancer. The cancer may be either a primary cancer or a metastatic cancer, or both. The cancer may include cells overexpressing a HER2/neu receptor protein.

In an embodiment, a drug delivery composition for treating a cancer in a subject may include: a polymerized carboxylic acid molecular scaffold and a plurality of biologically active molecular modules. The polymerized carboxylic acid molecular scaffold may include a poly-β-L-malic acid (PMLA). The plurality of biologically active molecular modules may include an antisense molecule that substantially inhibits synthesis of a HER2/neu receptor protein, a molecular module to facilitate delivery of the antisense molecule to cytoplasm, at least one antibody specific for the receptor protein that inhibits activity of the receptor protein, at least one antibody targeting a tumor vasculature protein, and a molecular module that prolongs circulation of the composition. The molecular modules may be covalently linked to the scaffold.

In an embodiment, a drug delivery composition for treating a cancer in a subject including: a polymerized carboxylic acid molecular scaffold and a plurality of biologically active molecular modules. The polymerized carboxylic acid molecular scaffold may be a poly-β-L-malic acid (PMLA). The plurality of biologically active molecular modules may include an antisense molecule that substantially inhibits synthesis of an epidermal growth factor receptor (EGFR/HER1) protein, an antisense molecule that substantially inhibits at least one subunit of laminin-411, a molecular module to facilitate delivery of the antisense molecule to cytoplasm, at least one antibody targeting a tumor vasculature protein, and a molecular module that prolongs circulation of the composition. The molecular modules may be covalently linked to the scaffold.

In an embodiment, a pharmaceutical composition is provided that includes a nanobiopolymeric conjugate of poly (β-L-malic acid) referred to as poly-β-L-malic acid or PMLA herein. PMLA may be covalently linked to an antisense molecule. The antisense molecule may be a functional module that inhibits expression of an oncogenic protein. The PMLA may be covalently linked to at least one module that is an antibody specific for the protein. The PMLA may optionally further comprise a module that is an antibody specific for an oncogenic vascular protein. The pharmaceutical composition may include a pharmaceutically acceptable carrier.

In an embodiment, the pharmaceutical composition may optionally further include one or more additional modules that are additional therapeutic agents. The additional therapeutic agent or agents may be selected from the group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences* Ed. by Gennaro, Mack Publishing, Easton, Pa., 1995 discloses various carriers used in formulating pharmaceutical compositions and known techniques for the preparation thereof. Materials which can serve as pharmaceutically acceptable carriers may include, but are not limited to, sugars, lactose, glucose, and sucrose; starches, corn starch and potato starch; cellulose and its derivatives, sodium carboxymethyl cellulose, ethyl cellulose, and cellulose acetate; powdered tragacanth; malt; gelatin; talc; excipients, cocoa butter and suppository waxes; oils, peanut oil, cottonseed oil, safflower oil, sesame oil, olive oil, corn oil, and soybean oil; glycols, a propylene glycol; esters, ethyl oleate and ethyl laurate; agar; buffering agents, magnesium hydroxide and aluminum hydroxide; alginic acid; pyrogen-free water; isotonic saline; Ringer's solution; ethyl alcohol, or phosphate buffer solutions. Pharmaceutically acceptable carriers may include non-toxic compatible lubricants, sodium lauryl sulfate and magnesium stearate. Pharmaceutically acceptable carriers may include coloring agents, releasing agents, coating agents, sweetening, flavoring and perfuming agents, preservatives and antioxidants.

In an embodiment, a kit for treating a patient having a cancer is provided. The kit may include a drug delivery composition. The drug delivery composition may include a nanobiopolymeric conjugate of a scaffold and molecular modules. The scaffold may be a poly-β-L-malic acid (PMLA). The molecular modules may include an antisense molecule that substantially inhibits synthesis or activity of a human epidermal growth factor receptor (HER) protein. The molecular modules may include a molecular module to facilitate delivery of the antisense molecule to cytoplasm. The molecular modules may include at least one targeting antibody specific for the HER protein. The molecular modules may include at least one antibody specific for a tumor vasculature protein. The molecular modules may include a molecular module that prolongs circulation of the composition. The PMLA may be covalently linked to the molecular modules. The drug delivery composition may be included in a container.

In an embodiment, the kit may further include a pharmaceutically acceptable buffer and instructions for use.

In an embodiment, a method for treating a cancer in a subject is provided. The method may include contacting the subject with a drug delivery composition. The drug delivery composition may include a poly-β-L-malic acid (PMLA) covalently linked to a plurality of molecular modules. The plurality of molecular modules may include at least one module that targets a tumorigenic cell or a cancer cell. The plurality of molecular modules may include at least one module that inhibits synthesis or activity of a human epidermal growth factor receptor (HER) protein in the cell. The HER protein may be selected from a group consisting of: HER1, HER2, HER3, and HER4. The plurality of molecular modules may include at least one module for cytoplasmic delivery. The drug delivery composition may be effective for inhibiting at least one of tumor growth, tumor regression and eliminating of cancer in a subject.

In an embodiment, the drug delivery composition may be further effective for inhibiting expression of cancer stem cell markers in the subject. The cancer stem cell markers may include at least one marker selected from the group consisting of: CD133 protein, c-myc protein, CD44 protein, Notch1 protein, and nestin protein. The inhibition of expression of cancer stem cell markers may indicate inhibition of growth of drug resistant tumors.

The method may also include analyzing at least one of: inhibition of tumor growth, tumor regression and elimination of cancer in the subject, thereby treating the cancer in the subject.

In an embodiment, the module that inhibits synthesis or activity of the HER protein may be at least one selected from the group consisting of: an antisense oligonucleotide (AON), an siRNA oligonucleotide, an antibody, a polypeptide, an oligopeptide and a low molecular weight drug. The AON may include a sequence complementary to an mRNA transcript of at least one protein selected from the group consisting of: HER2, an epidermal growth factor receptor (EGFR/HER1) protein, and a subunit of laminin-411. The sequence complementary to the HER2 mRNA transcript may include the following sequence: 5'AGGGAGCCGCA-GCTTCATGTCTGTG-3' (SEQ ID NO: 1). The sequence complementary to the HER2 mRNA transcript may include the following sequence 5'-CATGGTGCTCACTGCG-GCTCCGGC-3' (SEQ ID NO:2). The sequence complementary to the EGFR/HER1 mRNA transcript may include the following sequence: 5'-TCGCTCCGGCTCTCCCGAT-CAATAC-3' (SEQ ID NO:3).

In an embodiment, the subunit of laminin-411 may be selected at least one of α4 and β1 subunits. The α4 transcript sequence may include the following sequence: 5'-AGCT-CAAAGCCATTTCTCCGCTGAC-3' (SEQ ID NO:4). The β1 transcript sequence may include the following sequence: 5'-CTAGCAACTGGAGAAGCCCCATGCC-3' (SEQ ID NO:5).

In an embodiment, the siRNA oligonucleotide may include a sequence complementary to a gene encoding at least one of an epidermal growth factor receptor (EGFR/HER1) protein and HER2. The sequence complementary to a gene encoding EGFR/HER1 sequence may be selected from the group consisting of: 5'-CCUAUAAUGCUAC-GAAUAUtt-3' (SEQ ID NO:6), and 5'-AUAUUCGUAG-CAUUUAUGGag-3' (SEQ ID NO:7). The sequence complementary to a gene encoding HER2 may be selected from: 5'-GUUGGAUGAUUGACUCUGAtt-3' (SEQ ID NO:8), and 5'-UCAGAGUCAAUCAUCCAACat-3' (SEQ ID NO:9).

In an embodiment, the antibody may bind specifically to HER2/neu protein. The antibody may be Trastuzumab Herceptin®. The at least one module that targets the cell may include an antibody that binds specifically to a transferrin receptor protein. The antibody may be selected from at least one of: anti-human, rat anti-mouse, rat anti-human, rabbit anti-human and goat anti-human. The at least one module for cytoplasmic delivery may include an endosome escape unit. The endosome escape unit may be a leucine ethylester.

In an embodiment, the plurality of modules may further include a polyethylene glycol (PEG). The PEG may have a molecular weight of about 1,000 Da. The PEG may have a molecular weight of about 5,000 Da.

In an embodiment, the method may include analyzing inhibition of tumor growth. The step of analyzing may include observing more than about 60%, 70%, 80% or about 90% inhibition of tumor growth in the subject. The step of analyzing may include observing the inhibition of HER2/neu receptor signaling by suppression of Akt phosphorylation.

In an embodiment, the subject may be a mammal. The may be but is not limited to a human, a simian, an equine, a bovine, or a high value agricultural or zoo animal. The mammal may be a rodent. The rodent may be an experimental human-breast tumor-bearing nude mouse.

In an embodiment, the step of contacting may include administering the drug delivery to the subject. The drug delivery compositions may be formulated with an appropriate pharmaceutically acceptable carrier in a desired dosage. The drug delivery compositions may be administered to humans and other mammals topically. Topical administration may include drug delivery compositions formulated as powders, ointments, or drops. The drug delivery compositions may be administered orally, rectally, parenterally, intracisternally, intravaginally, intraperitoneally, or intravenously, depending on the severity and location of the cancer or other condition being treated. Intravenous administration may include injection as a bolus, or as a drip.

In an embodiment, dosage forms for topical or transdermal administration of the drug delivery compositions may include ointments, pastes, creams, lotions, gels, powders, solutions, sprays, inhalants, or patches. The drug delivery composition may be admixed under sterile conditions with a pharmaceutically acceptable carrier and any needed preservatives or buffers as may be required. Administration may be therapeutic or it may be prophylactic. Prophylactic formulations may be present or applied to the site of potential tumors, or to sources of tumors. The ointments, pastes, creams, and gels may contain, in addition to the drug delivery compositions, excipients. Excipients may be but are not limited to animal and vegetable fats, oils, waxes, paraffins, starch, tragacanth, cellulose derivatives, polyethylene glycols, silicones, bentonites, silicic acid, talc, zinc oxide, or mixtures thereof. Powders and sprays may contain, in addition to the drug delivery compositions, excipients. Excipients may include lactose, talc, silicic acid, aluminum hydroxide, calcium silicates, polyamide powder, or mixtures of these substances. Sprays may additionally contain customary propellants. Customary propellants may include chlorofluorohydrocarbons.

In an embodiment, the drug delivery composition may be administered using transdermal patches. The transdermal patches may have the added advantage of providing controlled delivery of the active ingredients to the body. Controlled delivery may be achieved using dosage forms. Dosage forms may be made by dissolving or dispensing the compound in the proper medium. Absorption enhancers may also be used to increase the flux of the drug delivery composition across the skin. The rate of delivery may be controlled by either providing a rate controlling membrane or by dispersing the compound in a polymer matrix or gel.

In an embodiment, the step of administering may include administering injectable preparations. The injectable preparations may include sterile injectable aqueous solutions or oleaginous suspensions formulated according to the known art using suitable dispersing or wetting agents and suspending agents. The sterile injectable preparation may be formulated as a sterile injectable solution, suspension or emulsion in a nontoxic parenterally acceptable diluent or solvent. The sterile injectable preparation may be formulated as a solution in 1,3-butanediol. The acceptable vehicles and solvents may include water, Ringer's solution, U.S.P. or isotonic sodium chloride solution. In addition, sterile, fixed oils may be employed as a solvent or suspending medium. Any bland fixed oil may be employed including synthetic mono- or diglycerides. In addition, fatty acids such as oleic acid may be used in the preparation of injectables. The injectable formulations may be sterilized. The injectable preparations may be sterilized by filtration through a bacterial-retaining filter, or by incorporating sterilizing agents in the form of sterile solid compositions which can be dissolved or dispersed in sterile water or other sterile injectable medium prior to use. To prolong the effect of a drug delivery composition, the absorption of the drug from subcutaneous or intramuscular injection may be slowed. Delayed absorption of a parenterally administered active agent may be accomplished by dissolving or suspending the drug delivery composition in an oil vehicle. Injectable depot forms may be made by forming microencapsule matrices of the drugs in biodegradable polymers such as polylactide-polyglycolide as described herein, and in Ljubimova et al., U.S. Pat. No. 7,547,511 issued Jun. 16, 2009, Ljubimova et al., U.S. patent application Ser. No. 12/473,992 published Oct. 22, 2009, Ljubimova et al., U.S. patent application Ser. No. 10/580,999 published Nov. 8, 2007, and Ding et al., International patent application PCT/US2009/40252 filed Apr. 10, 2009. The rate of active agent release is controlled by the ratio of active agent to polymer and the nature of the particular polymer employed. Examples of other biodegradable polymers include poly(orthoesters) and poly(anhydrides). Depot injectable formulations may also be prepared by entrapping the agent in liposomes or microemulsions which are compatible with body tissues.

In an embodiment, the drug delivery compositions may be used for rectal or vaginal administration. The drug delivery compositions may be administered as suppositories. Suppositories may be prepared by mixing the drug delivery compositions with suitable non-irritating excipients or carriers. The non-irritating excipients or carriers may include cocoa butter, polyethylene glycol or a suppository wax which are solid at ambient temperature but liquid at body temperature and therefore melt in the rectum or vaginal cavity and release the drug delivery compositions.

In an embodiment, the drug delivery composition may be administered for the treatment of a cancer associated with a particular receptor. The drug deliver composition may be administered in a therapeutically effective amount. The therapeutically effective amount may inhibit expression of at least one ligand of the receptor to a subject in need thereof. It will be appreciated that this encompasses administering an inventive pharmaceutical as a therapeutic measure to promote regression of a cancer or prevent further development or metastasis, or as a prophylactic measure to minimize complications associated with development of a tumor or cancer. As used herein, the "therapeutically effective amount" of the pharmaceutical composition is that amount effective for preventing further development of a cancer or transformed growth, and even to effect regression of the cancer. The drug delivery compositions may be administered using any amount and any route of administration effective for prevention of development of a cancer. Thus, the expression "amount effective for inhibiting expression or activity of the oncogenic protein", as used herein, refers to a sufficient amount of composition to prevent or retard development of a cancer, and even cause regression of a cancer or solid tumor. The cancer need not be limited to a solid tumor, and includes various types of lymphomas and leukemias.

In an embodiment, the exact dosage may be chosen by the individual physician with regard to the need of the patient to be treated. Dosage and administration may be adjusted to provide sufficient levels of the active agent(s) or to maintain the desired effect. Additional factors which may be taken into account include the severity of the disease state, e.g., cancer size and location; age, weight and gender of the patient; diet, time and frequency of administration; drug combinations; reaction sensitivities; and tolerance/response to therapy. Long acting pharmaceutical compositions might be administered every 3 to 4 days, every week, or once every two weeks depending on half-life and clearance rate of the particular composition.

In an embodiment, the drug delivery compositions may be formulated in dosage unit form for ease of administration and uniformity of dosage. The expression "dosage unit form" as used herein refers to a physically discrete unit of active agent appropriate for the patient to be treated. The total daily usage of the compositions of the present invention may be decided by the attending physician within the scope of sound medical judgment. For any drug delivery composition described herein, the therapeutically effective dose may be estimated initially either in cell culture assays or in animal models. Animal models may be mice, rabbits, dogs, or pigs as shown in Examples herein. The animal model may also be used to achieve a desirable concentration range and route of administration. Such information may then be used to determine useful doses and routes for administration in humans. A therapeutically effective dose refers to that amount of active agent, which ameliorates the symptoms or condition. Therapeutic efficacy and toxicity of active agents may be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions herein exhibit large therapeutic indices. The data obtained from the animal studies herein is used in formulating a range of dosage for human use.

In an embodiment, an initial dose of Herceptin® for human treatment accepted by the FDA may be 4 mg/kg followed by 2 mg/kg weekly for a total of 52 doses. An efficient dose of the composition herein for treatment of a mouse was 100 µl of observed 40 µg/ml, which may be equivalent to about 3.2 mg/kg for human use.

In an embodiment, the method may further include administering an additional therapeutic agent. The additional therapeutic agent may be selected from the group consisting of: an antibody, an enzyme inhibitor, an antibacterial agent, an antiviral agent, a steroid, a non-steroid-inflammatory agent, an antimetabolite, a cytokine, a cytokine blocking agent, an adhesion molecule blocking agent, and a soluble cytokine receptor.

In an embodiment, the method may include further administering antineoplastic agents. The antineoplastic agents may include agents for overcoming trastuzumab resistance. A variety of agents including monoclonal antibodies, recombinant proteins, and drugs, are known to have activity in treating breast cancer, and are here contemplated to be useful agents in combination with compositions described herein.

In an embodiment, the step of administering drug delivery composition including Herceptin® may include combining the drug delivery composition with other agents. The drug delivery composition may be administered with paclitaxel (taxol, Bristol-Myers Squibb) and docetaxel (taxotere, Sanofi-Aventis). The method may yield increases in response rates, time to disease recurrence, and overall survival (Esteva F J et al. 2002 J Clin Oncol. 20:1800; Slamon D J et al. 2001 N Engl J. Med. 344:783; Wardley A M et al. 2009. J Clin Oncol 49:976).

In an embodiment, the step of administering may include combining targeting of HER2 and other tyrosine kinases. Tyrosine kinases are associated with breast cancer tumorigenesis and are of substantial interest as potential drug targets (Ocana A et al. 2008 Clin Cancer Res 14:961). The insulinlike growth factor 1 receptor (IGF-1R), a receptor tyrosine kinase (RTK), has been shown to increase the growth of breast cancer cells and is also implicated in developing resistance to trastuzumab (Nahta. R et al. 2006 Nat Clin Pract Oncol 3:269). Cotargeting or simultaneous targeting of IGT-1R and HER2 may offer an advantage compared to targeting of the individual RTKs in breast cancer cells (Esparis-Ogando A et al. 2008 Ann Oncol 19:1860). The v-kit Hardy-Zuckerman 4 feline sarcoma viral oncogene homolog (c-KIT) RTK is overexpressed in triple-negative breast cancers (those that do not express estrogen receptor, progesterone receptor, and HER2) (Nielsen T O et al. 2004 Clin Res 10:5367). The activation of two nonreceptor cytosolic tyrosine kinases, c-abl oncogene 1 (ABL1) and c-SRC tyrosine kinase (CSK), is associated with the aggressiveness of breast cancer (Finn R S. 2008 Ann Oncol 19:1379) and proliferation of triple-negative breast cancers (Finn R S. 2008 Ann Oncol 19:1379; Finn R S et al. 2007 Breast Cancer Res Treat 105:319), respectively. Moreover, c-SRC has also been associated with antiestrogen resistance in estrogen receptor-positive breast tumors (van Agthoven T et al. 2009 J Clin Oncol 27:542).

The step of administering may include combining the drug delivery composition with Dasatinib, (Sprycel®, Bristol-Myers Squibb) a small-molecule tyrosine kinase inhibitor. Dasatinib targets the cytosolic c-SRC and ABM kinases, and RTKs c-KIT and platelet-derived growth factor receptors alpha and beta (Finn R S et al. 2007 Breast Cancer Res Treat 105:319; Rix U et al. 2007 Blood 110: 4055; Huang F, et al, 2007 Cancer Res 67: 2226; Huang F. et al. 2007 Cancer Res 67: 2226). The activity of Dasatinib for treatment of triple-negative breast cancer not expressing estrogen receptor, progesterone receptor, or HER2/neu (Finn R S et al. 2007 Breast Cancer Res Treat 105:319; Huang F. et al. 2007 Cancer Res 67: 2226), and favorable antitumoral activity in head and neck cancer in combination with gefitinib (Koppikar P et al. 2008 Clin Cancer Res 14:4284), led to combining trastuzumab and dasatinib for treatment of HER2-positive breast cancers. This combination was found to be highly effective against breast cancer cells overexpressing HER2 receptors. Both drugs individually inhibited cell proliferation in vitro and exhibited antitumoral action, and the combination resulted in a more potent effect on HER2-overexpressing cells.

In an embodiment, the drug delivery composition may be administered in combination with other drugs and may lead to decreased levels of phosphorylated HER2 and phosphorylated HEM, and a decrease observed in the total amount of these receptors. The combined treatment may affect downstream signaling routes, such as the ERK1 or AKT pathways that regulate cell proliferation and survival (Garcia-Echeverria C et al. 2008 Oncogene 27:5511; Roberts P J et al. 2007 Oncogene 26:3291). Dasatinib alone was as inhibitory for phosphorylated levels of ERK1 as the combined drug treatment. Treatment with Dasatinib also inhibited SRC or FAK phosphorylation to the same degree as the combined drug treatment. These two kinases are known targets of Dasatinib (Huang F. et al. 2007 Cancer Res 67: 2226) and participate in several oncogenic processes (Kim L C et al. 2009 Nat Rev Clin Oncol 6:587). Combined treatment and not the individual drugs was observed to decrease the level of phosphorylated AKT. Downstream targets of AKT such as p70S6K and BAD were also affected by the combined drug treatment, and not by the individual drugs, as the resting phosphorylated levels of these proteins were reduced by treatment with trastuzumab and dasatinib.

In an embodiment, the step of administering may include providing drug combination that may also induce caspase-independent apoptosis as determined by the lack of an effect of caspase inhibitors on apoptosis induced by the drug combination. One of the possible mediators in caspase-independent apoptosis is NAIF1 a protein that may be released from the mitochondrial intermembrane space by certain apoptotic stimuli. The release of NAIF1 from mitochondria to the cytosol, by treatment with the drug combination, may indicate that this mechanism could be responsible for caspase-independent apoptosis.

In an embodiment, the drug combination may also affect DNA repair machinery and lead to accumulation of double-stranded breaks (DSBs) which indicate control of DNA repair machinery by tyrosine kinases and potential clinical implications.

In an embodiment, the drug delivery composition may be administered in combination with Erlotinib (Tarceva, Roche), an inhibitor of EGFR. Erlotinib may block homologous recombination repair of the DSBs in breast cancer cells through reduction of RAD51 foci formation (Li L et al 2008 Cancer Res 68:9141). Previous studies have indicated that RTKs may regulate DNA repair (Tanaka T et al, 2008 Clin Cancer Res 14:1266; Ganaphthipillai S S et al. 2008 Cancer Res 68:5769).

In an embodiment, the drug delivery composition may be administered in combination with Gefitinib (Iressa, Astra Zeneca and Teva) is an EGFR inhibitor. Gefitinib may impede DNA repair in response to ionizing radiations in macrocytic lung cancer cells (Tanaka T et al., 2008 Clin Cancer Res 14:1266). Mutated forms of MET protein, an RTK implicated in several oncogenic processes such as invasion and metastasis (Benvenuti S et al, 2007 J Cell Physiol 213:316) or drug resistance (Engelman J A et al. 2007 Science 316:1039), have been reported to bind to and phosphorylate RAD51, facilitating DNA repair in tumor cells (Ganaphthipillai S S et al, 2008 Cancer Res 68:5769).

In an embodiment, a drug delivery composition may be administered with other drugs or agents. The agents may affect a transcription factor associated with Williams-Beuren syndrome (WSTF; also known as BAZ1B), a tyrosine kinase component of the WICH complex (WSTF-ISWI ATP-dependent chromatin-remodeling complex), that regulates the DNA damage response through phosphorylation of Tyr142 of H2AX (Xiao A et al. 2009 Nature 457:57).

It is here envisioned that drugs such as dasatinib in combination with other antineoplastic agents such as gefitinib and erlotinib (Koppikar P et al. 2008 Clin Cancer Res 14:4284), are further combined with drug delivery compositions described herein.

In an embodiment, the drug delivery composition may be administered in combination with Lapatinib (Tyverb®, GSK) is a dual EGFR/HER2 tyrosine kinase inhibitor (Rusnak D W et al. 2001 Mol Cancer Ther 1:85) which is highly selective to EGFR and HER2 (Karaman M W et al. 2008 Nat Biotechnol 26:127). In preclinical models of trastuzumab resistance, lapatinib inhibited phosphorylation of HER2 and overall growth in HER2 overexpressing breast cancer cell lines specifically chosen for extent of in vitro resistance to trastuzumab (Konechny G E et al. 2006 Cancer Res 66:1630). Further, treatment with lapatinib may be combined with trastuzumab and may result in a greater degree of survival and greater apoptosis induction than either agent alone (Xia et al. 2005 Oncogene 24: 6213). A substantial number of HER2-positive metastatic breast cancer patients treated with trastuzumab experience symptomatic central nervous system (CNS) metastasis, which unlike visceral diseases, are not well controlled by trastuzumab. Lapatinib and not trasuzumab has been shown to cross the blood-brain barrier, providing rationale for testing lapatinib in patients with CNS metastases (Nielsen D L et al. 2009 Cancer Treat Rev 35:121). Trastuzumab in combination with lapatinib may be to be superior to lapatinib alone in HER2-positive metastatic breast cancer patients (Blackwell K L et al. 2010 J Clin Oncol 28:1124).

In an embodiment, the drug delivery composition may be administered in combination with Pertuzumab (2c4, omnitarg, Genentech). Pertuzumab is a monoclonal antibody specific for the extracellular domain of HER2 protein. Pertuzumab may attach to a different epitope of HER2 compared to trastuzumab. Pertuzumab was observed to inhibit heterodimer formation between HER2 and EGFR or HER3 (Agus D B et al. 2002 Cancer Cell 2:127). Although the HER2/HER3 heterodimer may be important in HER2-driven cell signaling, the heregulin-dependent HER2/HER3 heterodimer may be disrupted by pertuzumab and may not be disrupted by trastuzumab (Jitunttila et al. 2009 Cancer Cell 15:429). In a phase II clinical trial involving combination treatment with pertuzumab and trastuzumab in HER2- positive breast cancer patients, treatment produced a response rate of 24.2%, and disease control rate of 50% (Baselga J et al. 2010 J Clin Oncol 28: 1138).

In an embodiment, the drug delivery composition may be administered in combination with Trastuzumab-DM1 comprised of trastuzumab and DM1, an agent that is an inhibitor of tubulin polymerization derived from maytansine. A stable MCC linker conjugates the DM1 to the trastuzumab. The compound may be designed to deliver DM1 to HER2-overexpressing cancer cells. Preclinical studies have indicated the growth-inhibitory effect of trastuzumab-DM1 in HER2-overexpressing and trastuzumab resistant cells (Lewis Phillips G D et al. 2008 Cancer Res 68:9280). In a phase II clinical trial involving HER2-positive metastatic breast cancer patients with disease progression despite trastuzumab-based therapy, trastuzumab-DM1 yielded an independently reviewed response rate and progression-free survival of 26.9% and 4.6 months, respectively (Vogel C L et al. 2009 J Clin Oncol 27: 15s (suppl; abstr 1017). Trastuzumab-DM1 had similar antitumor activity and an independently reviewed response rate of 24.2% even in patients previously treated with lapatinib and trastuzumab (n=66).

In an embodiment, the drug delivery composition may be administered in combination with PI3K pathway inhibitors. The PI3K pathway inhibitors may be used for treating HER2 expressing tumors. HER2-overexpressing breast cancer cells are believed to be dependent on the PI3K signaling pathway, and a number of genetic or epigenetic alterations in PI3K signaling molecules have been shown to cause resistance to trastuzumab or small-molecule HER2 kinase inhibitors. HER2-overexpression and PIK3CA mutations frequently occur simultaneously in breast cancer cells (Oda K et al. 2008 Cancer Res 68:8127), and cell lines with either HER2 amplification or PIK3CA mutation are equally Akt-dependent (She Q B et al. 2008 PLoS ONE 3:e3065). PI3K pathway inhibitors may therefore be useful in overcoming resistance to anti-HER2 agents. PI3K/mTOR dual inhibitor and Akt inhibitor were shown to effectively inhibit cellular growth in trastuzumab- and lapatinib resistant cells. At present, many classes of PI3K pathway inhibitors are in clinical development, and their roles in overcoming trastuzumab resistance will be tested in the future. These inhibitors may be used in combination with the drug delivery compositions herein.

In an embodiment, the drug delivery compositions may be administered in combination with inhibitors of alternative signaling molecules. The inhibitors of alternative signaling molecules may be used to treat trasuzumab resistant cancer cells. Alternative signaling from IGF-1R or MET may be associated with trastuzumab resistance. Small-molecular weight inhibitors of IGF-1R or MET receptor tyrosine kinase, and anti-IGF-1 antibody and anti-HGF antibody are in clinical development at present. Monotherapy or combination therapy with these agents and the drug delivery composition that includes trastuzumab may be therefore an attractive therapeutic strategy.

In an embodiment, the drug delivery compositions may be administered in combination with HER2 vaccines and adoptive immunotherapy targeting the HER2 extracellular domain tested in clinical trials. Results of these tests showed that significant levels of durable T-cell HER2 immunity may be generated with active immunization without significant consequences with regard to autoimmunity against normal tissues (Bernhard H et al 2002 Endoctr Relat Cancer 9:33). Early data from clinical trials testing the potential use of HER2-specific vaccines in adjuvant therapy for high-risk breast cancer patients show promising results (Peoples G E et al. 2008 Clin Cancer Res 14:797).

In an embodiment, the drug delivery composition may be administered in combination with Ertumaxomab (Rexomum, Fresenius Biotech GmbH, phase II study). Ertumaxomab is an intact bispecific antibody targeting HER2 and CD3 on T cells with preferential binding to activating Fcc type I/III receptors and redirecting T cells, macrophages, dendritic cells, and natural killer cells to HER2 expressing tumor sites (Kiewe P et al. 2008 Expert Opin Investig Drugs 17: 1553). In a phase I trial, ertumaxomab treatment was associated with one complete response, two partial responses, and two stable diseases in patients with metastatic breast cancer who had received extensive prior treatment (Kiewe P et al. 2006 Clin Cancer Res 12:3085). The effects of ertumaxomab are being evaluated in phase II studies.

In an embodiment, the drug delivery compositions may be administered using defucosylated trastuzumab. Defucosylated trastuzumab may be used to treat trastuzumab resistant cancer cells. Removal of fucose from antibody oligosaccharides attached to the heavy chain of $Asn^{297}$ (defucosylation) has been shown to significantly enhance antibody-dependent cellular cytotoxicity (ADCC) compared to the activity of regular antibodies. In addition, defucosylation of trastuzumab was also found to enhance ADCC in an in vitro assay as compared to regular trastuzumab (Suzuki E et al. 2007 Clin Cancer Res 13:1875). Defucosylated trastuzumab more than doubled the median progression-free survival compared with conventional trastuzumab in preclinical models of HER2-amplified breast cancer (Juntilla et al. 2010 Cancer Res 70: 4481).

Any of the above agents including paclitaxel, docetaxel, dasatinib, erlotinib, gefitinib, lapatinib, pertuzumab, trastuzumab, ertumaxomab, trasuzumab-DM1, defucosylated trastuzumab, PI3K pathway inhibitors and HER2 vaccines are here envisioned to be useful in combination with nano-biopolymer conjugate compositions herein to treat breast cancers by methods described herein.

In an embodiment, the drug delivery composition may include at least one module that targets a tumorigenic or a cancer cell to be selected from the group of agents consisting of: paclitaxel, docetaxel, dasatinib, erlotinib, gefitinib, lapatinib, pertuzumab, trastuzumab, ertumaxomab, trasuzumab-DM1, defucosylated trastuzumab, PI3K pathway inhibitors and HER2 vaccines.

In an embodiment, the step of contacting the subject with the composition may further include providing the composition in a unit dose effective for treatment the cancer in the subject. For example, the effective dose may be at least one dose selected from the group consisting of: 1 µg/kg, 50 µg/kg, 100 µg/kg, 200 µg/kg, 300 µg/kg, 400 µg/kg, 500 µg/kg, 600 µg/kg, 700 µg/kg, 800 µg/kg, 900 µg/kg, 1 mg/kg, 50 mg/kg, 100 mg/kg, 200 mg/kg, 300 mg/kg, 400 mg/kg, 500 mg/kg, 600 mg/kg, 700 mg/kg, 800 mg/kg, 900 mg/kg, and 1 g/kg In an embodiment, of the cancer may be selected from the list consisting of: gastric, endometrial, salivary gland, lung, non-small cell lung, pancreatic, ovarian, peritoneal, prostate, colorectal, breast, cervical, uterine, ovarian, brain, head and neck, testicular and teratoma cancers.

The cancer may be either a primary cancer, or a metastatic cancer, or both.

As discussed above and described in greater detail in the Examples, inhibition of expression or activity of an oncogenic protein may be useful to prevent development or metastasis of a cancer conditions. These inhibitors may be clinically useful in preventing further growth of a particular cancer type, including but not limited to the breast cancer; skin cancer; ovarian cancer; cervical cancer; the retinoblastoma; colon cancer and other conditions, e.g., those arising from the lining of the gastrointestinal tract; lung cancer and cancers of the respiratory tract; renal carcinoma and other tumors arising from the inner surface of kidney tubules; leukemias and lymphomas and disorder of blood; and other types of genital cancer including those associated with various strains of papilloma virus; brain tumors; and cancers of the uterus, of the vagina, of the urethra.

In an embodiment, the diagnostic, prognostic and therapeutic methods described herein may not be limited to treating conditions in humans, but may be used to treat similar conditions in any mammal. The mammal may be but not limited to bovine, canine, feline, caprine, ovine, porcine, murine, or equine species. When treating tumors in a given species, it is preferred, but not required, that the antisense oligonucleotides have a nucleotide sequence that is substantially identical in base sequence to that as it occurs naturally in the species.

The invention having been fully described is it further exemplified in a research paper by Satoshi Inoue et al. entitled "Polymalic acid-based nanobiopolymer provides efficient systemic breast cancer treatment by inhibiting both HER2/neu receptor synthesis and activity", which was published Feb. 15, 2011 in Cancer Research 71(4): 1454-1464, and is incorporated herein by reference as if fully set forth. A skilled person will recognize that many suitable variations of the methods may be substituted for or used in addition to those described above and in the claims. It should be understood that the implementation of other variations and modifications of the embodiments of the invention and its various aspects will be apparent to one skilled in the art, and that the invention is not limited by the specific embodiments described herein and in the claims. The present application mentions various patents, scientific articles, and other publications, each of which is hereby incorporated in its entirety by reference.

Further embodiments herein may be formed by supplementing an embodiment with one or more element from any one or more other embodiment herein, and/or substituting one or more element from one embodiment with one or more element from one or more other embodiment herein. Further embodiments herein may be described by reference to any one of the appended claims following claim 1 and reading the chosen claim to depend from any one or more preceding claim.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below Example 1

Experimental Design

Compositions and methods of the present invention provide a nanobiopolymeric drugs based on poly-β-L-malic acid (PMLA) platform specifically designed for delivery into HER2/neu-positive tumors. Targeted nanobiopolymeric conjugates based on poly-β-L-malic acid (PMLA) are biodegradable, non-toxic, and non-immunogenic. The PMLA nanoplatform was synthesized for repetitive systemic treatments of HER2/neu-positive human breast tumors in a xenogeneic mouse model. Various moieties were covalently attached to PMLA, including a combination of morpholino antisense oligonucleotides (AON) directed against HER2/neu mRNA, to block HER2/neu synthesis; anti-HER2/neu antibody trastuzumab (Herceptin®), to target breast cancer cells and inhibit receptor activity simultaneously; and transferrin receptor antibody, to target the tumor vasculature and mediate delivery of the nanobiopolymer through the host endothelial system.

The Examples herein include tests of the lead compound, and data show that this compound significantly inhibited growth of HER2/neu-positive breast cancer cells in vitro and in vivo, and enhanced apoptosis and inhibition of HER2/neu receptor signaling with suppression of Akt phosphorylation was observed in treated cells and animals. In vivo imaging analysis and confocal microscopy demonstrated selective accumulation of the nanodrug in tumor cells as a result of an active delivery mechanism resulting from design of the lead compound. Systemic treatment of human breast tumor-bearing nude mice resulted in more than 90% inhibition of tumor growth and tumor regression, compared to partial (50%) tumor growth inhibition in mice treated with control trastuzumab alone or control AON alone, either free or attached to PMLA. Data from Examples herein offer a preclinical demonstration of use of the PMLA nanoplatform for combination cancer therapy.

The epidermal growth factor receptor or ErbB family of receptor tyrosine kinases is exemplified by an epidermal growth factor receptor (also called HER1 or ErbB1), HER2 (ErbB2 or neu), HER3 (ErbB3), and HER4 (ErbB4). Upon ligand binding, ErbB family members form homodimers and heterodimers followed by the phosphorylation within intracellular kinase domains (Yarden et al. 2001 Nat Rev Mol. Cel Biol 2:127). Upon ErbB1 and ErbB2 activation, phosphotyrosylated sites in Src-homology 2 (SH2) domains in these proteins serve as docking sites for adaptor proteins such as Shc, Grb2, and Sos resulting in the activation of the of Ras/Raf/mitogen-activated protein kinase (MAPK) kinase (MEK)/MAPK and PI3K/protein kinase B (PKB) pathways and promotion of proliferation and mitogenesis (Yarden et al. 2001 Nat Rev Mol Cel Biol 2:127).

The HER2/neu proto-oncogene, also known as erbB-2, encodes a 185-kDa type I transmembrane receptor tyrosine kinase that is member of the epidermal growth factor receptor family (Hynes N E et al., 2005 Nat Rev Cancer 5:341; Bargmann C I et al. 1986. Nature 319:226; Coussens L et al. 1985 Science 230:1132). Early studies have identified HER2/neu protein overexpression in several human carcinomas, including subsets of ovarian and breast cancers (Hynes N E et al. 1994. Biochim Biophys Acta 1198:165; D'Emilia J et al. 1989 Oncogene 4:1233; Slamon D J et al. 1989 Science 244:707). HER2/neu overexpression has been linked to a short relapse time and poor survival of breast cancer patients (Slamon D J et al. 1987 Science 235:177), as this protein plays a role in the molecular mechanisms of human cancers.

The ErbB2 gene is amplified and overexpressed in up to 30% of primary breast cancers and this is associated with poor patient prognosis (Slamon D J et al., 1989 Science 244:707). ErbB1 is also overexpressed in up to 30% of primary invasive breast cancers and this is correlated with reduced overall survival, proliferation, and higher metastatic potential (Tsutsui S et al. 2002 Breast Cancer Res Treat 71:67). Inhibition of ErbB1 signaling reduces both ErbB1 and ErbB2 activity and delays tumorigenesis in MMTV/Neu mice (Lenferink A E G et al. 2000 Proc Natl Acad Sci 97:9609). The cooperative activation of proliferative pathways by these two receptors has stimulated the development of a number of small molecule inhibitors of members of the ErbB family for use as anticancer agents.

Newly diagnosed estrogen positive breast cancers are commonly treated with the antiestrogen agent tamoxifen. In estrogen-positive breast cancers, overexpression of both Erb1 and Erb 2 is associated with resistance to tamoxifen therapy. It was shown that administration of such anticancer agents as lapatinib (GW572016) and tamoxifen together was advantageous and restored tamoxifen-mediated cell cycle arrest and inhivited tamoxifen-resistant breast tumor growth (Chu I et al. 2005 Cancer Res 65:18).

Characteristics such as extracellular accessibility, high expression, and association with poor prognosis make HER2/neu an attractive candidate for antibody therapy. Metastatic breast cancer patients are currently being treated with Trastuzumab (also known as Herceptin; Genentech, Inc., San Francisco, Calif.), a Food and Drug Administration-approved humanized monoclonal anti-HER2/neu (Kaptain S et al. 2001 Diagn Mol Pathol 10:139). Breast cancer clinical trials for patients with advanced disease expressing high levels of HER2/neu showed that use of Trastuzumab as a single immunotherapeutic agent resulted in an objective response rate of 12% to 26% (Cobleigh M A et al. 1999 J Clin Oncol 17:2639; Baselga J et al. 1996 J Clin Oncol 14:737; Vogel C L et al. 2002 J Clin Oncol 20:719). Subsequent clinical trials in patients with advanced disease have also shown that targeting metastatic breast cancer with Trastuzumab in combination with chemotherapy resulted in a 50% objective response, but disease relapse still affected most cases (Slamon D J et al. 2001 N Engl J Med 344:783). In addition, Trastuzumab lacks considerable activity against tumors expressing HER2/neu that are not of breast origin (Burstein H J 2005 N Engl J Med 353:1652). Furthermore, resistance to Trastuzumab is a growing problem in patients with breast tumors. Novel treatments for patients with HER2/neu-expressing tumors are still needed.

In 66% to 88% of cases, HER2/neu-overexpressing tumors demonstrate primary resistance to Herceptin® (Baselga J et al. 1999 Semin Oncol 26:78; Nahta R et al. 2004 Cancer Res. 64:398). This resistance may be due to epitope masking by overexpressing mucins, loss of receptor ability to influence pro-survival signaling through PI3K-Akt axis, or loss of protein phosphatase PTEN leading to the activation of PI3K-Akt signaling (Tseng P H et al. 2006 Mol Pharmacol 70:1534-41; Nagy P et al 1998 Cytometry 32:120; Tanner M et al. 2004 Cancer Ther. 3:1585-92).

Nanobiopolymers as a Platform for Carrying Multiple Drugs for Treatment of HER2/Neu Cancers Advantages of drug combinations can be offered in a single molecular entity such as a nanobiopolymeric conjugate. These compounds offer enhanced cancer cell specificity because of the presence of tumor targeting antibodies, bypass drug resistance by delivering polymer-bound drugs into cancer cell cytoplasm, and can carry multiple drugs on a single platform (Wu K et al. 2010 Angew Chem Int Ed Engl. 9:1451). Efficient delivery of nanobiopolymer-attached drugs to tumors is increased by passive targeting through enhanced permeability and retention (EPR) effect typical for tumors (Maeda H et al. 2009 Eur J Pharm Biopharm 71:409), and additionally, by active targeting using antibodies, such as anti-TfR (Maeda H et al. 2009 Eur J Pharm Biopharm 71:409; Liu X, et al. 2008 Cancer Gene Ther. 15:126; Peterson C M et al. 2003 Adv Exp Med Biol. 519:101). Table 1 shows the size (smaller than 30 nm) of conjugates used in Examples herein.

The slightly negative ζ potentials promote interaction of the conjugate with the cell membrane and enhance intracellular internalization (Wilhelm C et al. 2003 Biomaterials 24:1001-11).

A general problem with anti-cancer drugs is lack of specific tumor targeting, resulting in an extent of random tissue accumulation and significant side effects for normal tissues (Shukla R et al. 2008 Nanotech 19:1; Shukla R et al. 2006 Bioconjug Chem 17:1109). To circumvent this drawback, tumor-targeting antibodies have been used as drug carriers or directly as therapeutics (e.g., Herceptin®). Dendrimer nanoconjugates with attached Herceptin® displayed enhanced accumulation in breast cancer cells in animal models (Shukla R et al. 2006 Bioconjug Chem 17:1109). Methotrexate-loaded dendrimers produced a cytotoxic effect in tumor cells in vitro resulting from Herceptin®-mediated complex internalization (Shukla R et al. 2008 Nanotech 19:1). However, the efficacy of these nanodrugs was limited because of lack of efficient endosome release unit (Shukla R et al. 2008 Nanotech 19:1). Drugs were specifically delivered to cancer cells and tumor growth was inhibited as was angiogenesis in brain glioma-bearing animals (Fujita M et al. 2006 Angiogenesis 9:183; Ljubimova J Y et al. 2008 Chem Biol Interact. 171:195). The efficiency of the polymers was associated with properties of tumor targeting, use of AON drugs to more than one tumor marker at the same time, and the presence of endosome disruption moiety ensuring drug release inside the target cell (Gasslmaier B et al. 2000 Eur J Biochem 267:5101).

Table 1 summarizes nanobiopolymer drugs synthesized for use in Examples herein.

TABLE 1

Nanobiopolymer drugs and controls for treatment of cancers overexpressing HER2/neu, molecular sizes, and ζ potentials

| Nanobiopolymer variant | Version | Size (nm) | ζ potential (mV) |
|---|---|---|---|
| P/mPEG/LOEt/AON/Herceptin ®/TfR(M) | Lead drug with AON, Herceptin ® and TfR(M) | 22.1 (±2.3) | −5.2 ± (0.4) |
| P/mPEG/LOEt/AON/TfR(H/M) | with AON and TfR (Human/Mouse) | 20.1 (±2.4) | −5.7 (±0.6) |
| P/mPEG/LOEt/Herceptin ® | with Herceptin ® alone | 15.1 (±1.2) | −4.1 (±0.4) |
| P/mPEG/LOEt/IgG | Control version for imaging study with IgG | N/A | N/A |

PMLA is a natural polymer obtained from the slime mold *Physarum polycephalum* (Lee B S et al. 2006 Bioconjug Chem 17:317; Lee B S et al. 2002 Water-soluble aliphatic polyesters:poly(malic acid)s, in: Doi YSA, eds, Biopolymers, Weinheim: Wiley-VCH, 2002 pp. 75-103). PMLA is non-toxic, non-immunogenic, and biodegradable in vitro and in vivo, stable in the bloodstream, and highly water-soluble (Gasslmaier B et al. 1997 Eur J Biochem 250:308; Gsslmeier B et al. 2000 Eur J Biochem 267:5101). Systemic delivery of morpholino AONs having nucleotide sequences specific to α4 and β1 chains of a tumor vasculature-specific protein, laminin-411 (formerly, laminin-8), to intracranial glioblastoma was shown to result in marked inhibition of tumor angiogenesis and growth (Ljubimova J Y et al. 2008 Nanomedicine 3:247; Ding H et al. 2010 Proc Natl Acad Sci online publication). Further, to target tumor vasculature, a mAb to transferrin receptor (TfR) was attached to the same nanoplatform. The nanobiopolymer composition carrying each of anti-HER2/neu antibody (Herceptin®), anti-TfR antibody, and AON to HER2/neu is shown herein to enhance the specificity and anti-tumor effect towards HER2/neu positive breast cancer. Without being limited by any specific theory or molecular mechanism, the lead compound tested herein is a nanoplatform designed to work on several molecular levels, to inhibit the synthesis of new HER2/neu receptors with AON, and to block the activity of existing HER2/neu on the tumor cell membrane with Herceptin®.

Antisense oligonucleotides (AONs) that bind specifically to mRNA and block protein synthesis are tools specific for silencing gene expression. Efficient delivery of AONs and siRNAs in systemic treatment of tumors however still presents significant problems (Patil S D et al. 2005 AAPS 7:E61; Thierry et al., 2003 Curr Opin Mol Ther 5:133). Preclinical studies of AON for cancer treatment showed promising results, and stability of AON in plasma renders these molecules feasible for systemic treatment (Busch R K et al. 1994 Cancer Lett 86:151; Sekhon H S et al. 2008 Lung Cancer 60:347; Garbuzenko O B et al. 2010 Proc Natl Acad Sci 107:10737). Further, Morpholino AONs specific for dystrophin have been delivered to dystrophic muscle cells in vivo in a Duchenne muscular dystrophy mouse model and to patients (Wu B et al. 2010 Gene Ther 17:132; Kinali M et al 2009 Lancet Neurol 8:918). An AON specific for HER2/neu was observed to be more potent for inhibiting neoplastic cell proliferation in vitro than mAb inhibition of HER2/neu receptor (Roh H et al. 2000 Cancer Res 60:560). Combination treatment of HER2/neu-positive breast cancer cells in vitro with HER2/neu AON and conventional chemotherapeutic agents results in synergistic inhibition of tumor cell growth by activation of apoptosis (Rait A S et al. 2001 Cancer Gene Ther 8:728; Lewis P G D 2008 Cancer Res 68:9280).

Nanoparticles are used in drug delivery as carriers for small and large molecules. Nanoparticles are defined as particulate dispersions or solid particles with a size in the range of 10-1000 nm. The drug is dissolved, entrapped, encapsulated or attached to a nanoparticle matrix (Langer R. 2000 Acc Chem Res 33:94). Nanobiopolymers of the present invention differ from nanoparticles in that nanoparticles have no covalent bonds between the particle and drug cargo, generally merely leak the drug, and accordingly cannot directly transport cargo to and release the cargo inside tumor cells.

Contrary to nanoparticles, nanobiopolymer compositions provided herein comprise a single unitary molecular entity having functional modules including a plurality of the following: tumor cell-targeting antibodies, two or more anti-tumor drugs, an endosomal disruption moiety, and a glutathione-cleavable bond to release the drug inside tumor cell cytoplasm, covalently attached. Such a construct functions to eliminate leakiness, suppresses non-tumor accumulation thereby minimizing side effects, and increase drug half-life dwell time of the composition in plasma. As a result, tumor uptake and drug specificity were observed in examples herein to be enhanced, leading to a significant reduction of tumor growth and volume. Moreover, the combined drug action through inhibiting Akt activation and increase of tumor cell apoptosis was also observed in examples herein.

Nanobiopolymers of the present invention offer a great potential in cancer therapy.

Example 2

Reagents

Morpholino™-3′-NH$_2$ antisense oligonucleotides (AONs) used in Examples herein were custom made by Gene Tools (Philomath, Oreg.).

AONs specific for HER2/neu included two sequences:

version 1:   5′-AGGGAGCCGCAGCTTCATGTCTGTG-3′ (SEQ ID NO: 1), and version 2:   5′-CATGGTGCTCACTGCGGCTCCGGC-3′ (SEQ ID NO: 2).

AONs specific for an epidermal growth factor receptor (EGFR) included:

5′-TCGCTCCGGCTCTCCCGATCAATAC-3′ (SEQ ID NO: 3).

AONs specific for α4 and β1 subunits of laminin-411 included:

α4 subunit:   5′-AGCTCAAAGCCATTTCTCCGCTGAC-3′ (SEQ ID NO: 4), and

β1 subunit:   5′-CTAGCAACTGGAGAAGCCCCATGCC-3′ (SEQ ID NO: 5).

siRNA specific for EGFR included sequences as follows:

sense:      5′-CCUAUAAUGCUACGAAUAUtt-3′ (SEQ ID NO: 6), and antisense:  5′-AUAUUCGUAGCAUUUAUGGag-3′ (SEQ ID NO: 7).

siRNA specific for HER2 receptor protein included:

sense:      5′-GUUGGAUGAUUGACUCUGAtt-3′ (SEQ ID NO: 8), and antisense:  5′-UCAGAGUCAAUCAUCCAACat-3′ (SEQ ID NO: 9).

Small letters "tt", "ag" and "at" at the 3′-terminus of the siRNA sequence denote DNA oligonucleotides that are synthesized to anneal siRNA to a DNA molecule.

Highly purified, endotoxin-free poly-β-L-malic acid, Mw (weight-averaged)=100 kDa, polydispersity=1.1, was obtained from the culture broth of *Physarum polycephalum*. Rat anti-mouse TfR mAb R17217 (mTfR) was purchased from Southern Biotech (Birmingham, Ala.). Cysteamine (2-mercaptoethyl-1-amine hydrochloride), N-hydroxysuccinimide, other reagents and solvents were of highest available purity and purchased from Sigma-Aldrich (St. Louis, Mo.).

Example 3

Synthesis of Polymalic Acid Nanobiopolymers

The nanobiopolymers contain five to six components: PMLA as the backbone; functional modules include: morpholino AON to inhibit HER2/neu protein synthesis; targeting anti-TfR mAb; anti-tumor Herceptin®; 40% leucine ethyl ester (LOEt) as endosome escape unit to achieve cytoplasmic AON delivery, and 5% PEG$_{5000}$ to increase stability in the bloodstream. FIG. 1 illustrates a chemical structure and schematic drawings showing a nanobiopolymeric conjugate designed to inhibit HER2/neu expression by antisense oligonucleotides (AON) and to attenuate HER2/neu-mediated cell signaling by Herceptin®. The modules are HER2/neu morpholino AON (indicated 1 in Figure) conjugated to the PMLA scaffold by disulfide bonds (S—S) that are cleaved by cytoplasmic glutathione to release the free drugs; targeting and/or effector antibodies that include antibody specific to a transferrin receptor protein (TfR) either alone or in combination with monoclonal antibodies (mAbs) to mouse TfR (indicated 2a in Figure), human TfR (indicated 2b) and Herceptin® (indicated 2c) for tumor endothelial and cancer cell targeting, receptor-mediated endocytosis, and anti-tumor effect, polyethylene glycol (PEG) for drug protection (indicated 3), stretches of conjugated L-leucine ethyl ester (LOEt) for endosomal escape of the drug (indicated 4), and optional fluorescent reporter dye (Alexa Fluor 680) for imaging (indicated 5). The nanopolymer also contained free unsubstituted pendant carboxyl groups for enhancing solubility and nonfunctional disulfides originating from chemical masking of excess sulfhydryls with 3-(2-pyridyldithio)-propionates.

Referring to FIG. 1, anti-mouse TfR mAb on Herceptin®-containing conjugate was used to target tumor vasculature. The conjugate with AON without Herceptin® included an anti-human TfR mAb attached to it to promote drug binding to human tumor cells and its internalization. The preconjugate containing 40% LOEt, 5% PEG$_{5000}$ and 10% of cysteamine (% referring to the total amount of pendant carboxyl groups in polymalic acid) was synthesized by the methods described previously (Lee B S et al. 2006 Bioconjug Chem 17:317). The antibodies conjugated with the preconjugate were qualitatively and quantitatively assayed by size exclusion HPLC. ELISA with purified TfR and HER2/neu was used to assess functional reactivity of attached antibodies as described (Fujita M et al. 2007 J Control Release. 122:356).

Conjugates for imaging were fluorescently labeled with Alexa Fluor® 680 C2-maleimide (Invitrogen, Carlsbad, Calif.) by forming thioether with sulfhydryl groups. Antibody conjugates were then reacted with HER2/neu AON (FIG. 1). A control conjugate contained Herceptin® (FIG. 1) and not HER2/neu-specific AON.

Example 4

The Nanobiopolymer Characterization

Chemical and physical characterization of polymeric nanobioconjugate was performed by various methods including L-malate dehydrogenase assay after nanobiopolymer hydrolysis at 100° C. in the presence of 6 M HCl, PEG colorimetric determination and protein quantification, size and ζ potential, HPLC, and ELISA. HPLC was performed on a Hitachi analytical Elite LaChrom HPLC-UV system (Hitachi, Pleasanton, Calif.) and size exclusion, on a Bio-Sep-SEC-S 3000 column (Phenomenex, Torrance, Calif.). The nanobiopolymer variants were characterized by their size (hydrodynamic diameter) on the basis of noninvasive back-scattering (NIBS), and ζ potential from electrophoretic mobility based on the Helmholtz-Smoluchowski formula, using electrophoresis M3-PALS (Gasslaier B et a. 1997 Eur J Biochem 250:308). Both measurements were performed in a Zetasizer Nano System ZS90 (Malvern Instruments, Malvern, UK). Data on molecular size and ζ potential represent mean±standard deviation obtained from three independent measurements.

Example 5

Cell Lines and Culture Conditions

Human breast cancer cell lines BT-474, SKBR-3, MDA-MB-231, MDA-MB-435, MDA-MB-468, and MCF-7 were obtained from American Type Culture Collection (Manassas, Va.). BT-474, MDA-MB-231, MDA-MB-435, MDA-MB-468, and MCF-7 were cultured in DMEM with 10% fetal bovine serum and antibiotics. SKBR-3 was cultured in McCoy's 5A medium with 10% fetal bovine serum and antibiotics.

Example 6

Nomenclature

The term "nanobiopolymer" denotes a drug delivery system with PMLA as a nanoplatform and functional module groups covalently attached to the PMLA, including an AON, a rat anti-mouse or a mouse anti-human targeting TfR mAbs (M and H, respectively), and LOEt as the endosomal escape unit module. The nanobiopolymer drugs (FIG. 1 and Table 1) described herein to treat HER2/neu-positive breast cancer contained either a drug HER2/neu AON or drug Herceptin® or both HER2/neu AON+Herceptin®.

Example 7

Cell Proliferation Assay

HER2/neu-overexpressing breast cancer cells each of BT-474 or SKBR-3 were seeded into six-well plates at $3 \times 10^5$ cells/well. The next day, cells were treated with one of Endoporter (4 μM; control); Herceptin (40 μg/ml); P/mPEG/LOEt/Herceptin® (40 μg/ml); Endoporter (4 μM) and AON (4 AI); P/mPEG/LOEt/AON/TfR(H/M); P/mPEG/LOEt/AON/Herceptin®/TfR(M); and PBS control. Seventy-two hours after treatment, the cells were stained with Trypan Blue. Cell viability was determined by calculating the mean of cell counts for each treatment group (in triplicate) and was expressed as a percentage of the total number of cells treated normalized to the number of cells treated with PBS.

Example 8

Western Blotting

BT-474 and SKBR-3 breast cancer cells were treated with Herceptin® (40 μg/ml); P/mPEG/LOEt/Herceptin® (40 μg/ml equivalent to Herceptin®); Endoporter (4 μM) and AON (4 μM); P/mPEG/LOEt/AON/TfR(H/M); P/mPEG/LOEt/AON/Herceptin®/TfR(M); PBS control, or 4 μM Endoporter. Cell lysates were collected after 72 hours and were analyzed by western blotting as described previously (Inoue S et al. 2005 Mol. Ther. 12:707-15). Lysates of excised breast tumors after various treatments were analyzed by these methods. The following anti-human primary antibodies were used: HER2/neu, Akt, phosphorylated Akt (p-Akt), glyceraldehyde 3-phosphate dehydrogenase (GAPDH, to normalize gel load) (all from Cell Signaling Technology, Beverly, Mass.), and poly(ADP ribose) polymerase (PARP; BD Biosciences, San Jose, Calif.).

Example 9

Tumor Xenografts in Nude Mice

Animal experiments were performed in accordance with the protocols approved by the Cedars-Sinai Medical Center Institutional Animal Care and Use Committee. Athymic mice (CrTac: NCr-Foxn1nu Homozygous; Taconic, Hudson, N.Y.) were used. A 0.72-mg, 90-day release, 17β-estradiol pellet (Innovative Research of America, Sarasota, Fla.) was inserted subcutaneously into the back of each mouse seven days prior to injection. An amount of $1 \times 10^7$ BT-474 cells suspended in 150 µl of Matrigel (BD Biosciences, Bedford, Mass.) were injected into the right flank of each of 35 mice (5 mice per group), and treatment was initiated when tumors achieved an average size of >120 mm$^3$ (21 days after injection). Mice were divided into five treatment groups and each group was administered either of: sterile PBS (control); Herceptin® (40 µg/ml); P/mPEG/LOEt/Herceptin® (40 µg/ml equivalent to Herceptin®); P/mPEG/LOEt/AON/TfR (H/M); or P/mPEG/LOEt/AON/Herceptin®/TfR(M); into the tail vein twice a week. Treatments were performed six times during a period of three weeks.

Tumor xenografts were measured with calipers twice a week, and tumor volumes were determined using the formula: (length×width$^2$)×(π/6).

Eighteen days after the last treatment, the animals were anesthetized with 3% isoflurane-air mixture and were euthanized. Tumor samples were stained with hematoxylin and eosin for morphological observation. The data are the average of two independent examples.

Example 10

Confocal Microscopy

Alexa Fluor 680-labeled nanobiopolymers (P/mPEG/LOEt/IgG, control); P/mPEG/LOEt/Herceptin®, 40 µg/ml; or P/mPEG/LOEt/AON/Herceptin®/TfR(M)) was each injected into the tail vein of mice. Twenty-four hours after drug administration, mice were euthanized; the tumors were harvested to detect the fluorescent signal, snap-frozen in liquid nitrogen and embedded in OCT compound for confocal microscopy (TCS SP5x microscope; Leica Microsystems, Mannheim, Germany).

Example 11

In Vivo Imaging

BT-474 human breast cancer cells were implanted into the right thigh of mice as described. When tumor size attained 120 mm$^3$, 160 µl of Alexa Fluor 680 labeled nanobiopolymers was injected intravenously (4 µM). P/mPEG/LOEt/IgG was used as a negative control. Drug distribution and localization was assessed in tumor-bearing mice using Xenogen IVIS 200 imager (Caliper Life Sciences, Hopkinton, Mass.), at different time points before drug administration, 1 h, 3 h, 6 h, and 24 h after the drug injection). Twenty-four hours after drug administration, mice were euthanized and the circulating drugs eliminated by intraarterial PBS perfusion. The tumor and major organs were harvested to detect the fluorescent signal.

Example 12

Statistical Analysis

Student's t-test (for two groups) and analysis of variance (ANOVA, for three and more groups) were used to calculate significance of the experimental results. GraphPad Prism4 program (GraphPad Software, statistical San Diego, Calif.) was utilized for all calculations. Data are presented as mean±standard error of mean (SEM). The significance level was set at $P<0.05$.

Example 13

Synthesis of Polymer Conjugates

Of the HER2/neu-specific AON sequences, a version that did not inhibit HER2/neu expression well in comparison with another version was observed; therefore, only the effective version was conjugated to the polymer platform. The absolute molecular weight of the lead version of nanobiopolymer (FIG. 1) was 1,300 kDa by light scattering and close to the calculated value based on design. Hydrodynamic diameters (nano sizes) and ζ potentials of the nanobiopolymers in FIG. 1 are summarized in Table 1. Parameters for ζ potentials in the range of −4.1 to −5.7 mV have been reported for other nanoparticles as compatible with cell membrane attachment and nanoparticle internalization (Lorenz M R et al. 2006. Biomaterials 27:2820; Wilhelm C et al. 2003 Biomaterials. 24:1001).

Example 14

Figure 2:
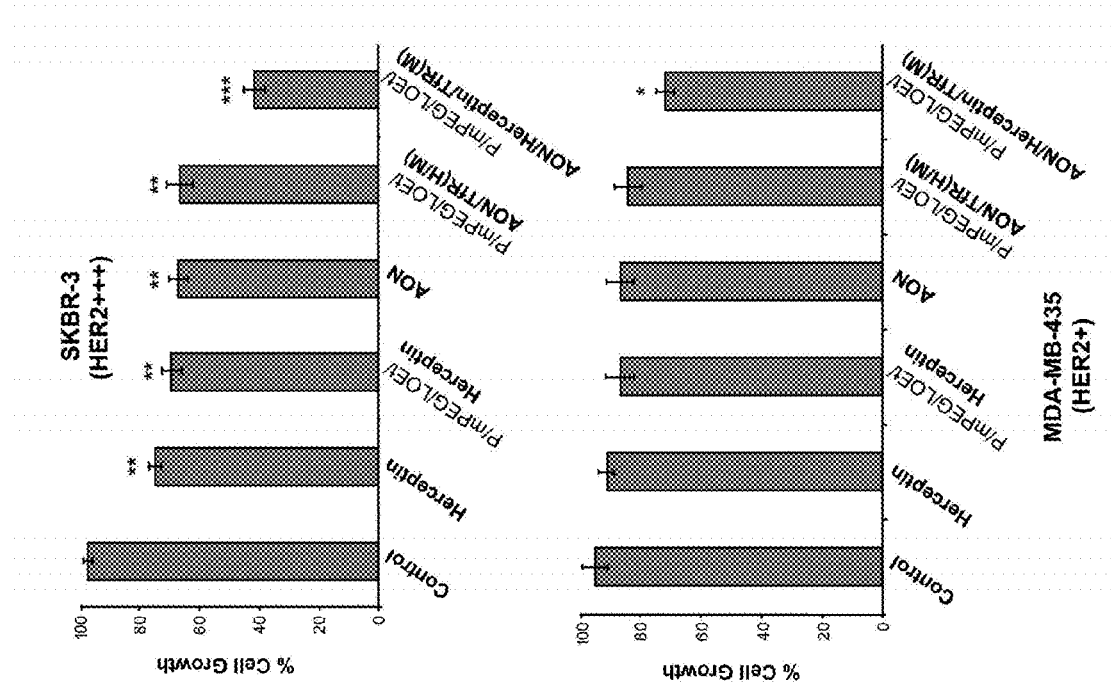
FIG. 2 illustrates data obtained from an in vitro cell viability assay.
Figure 2:
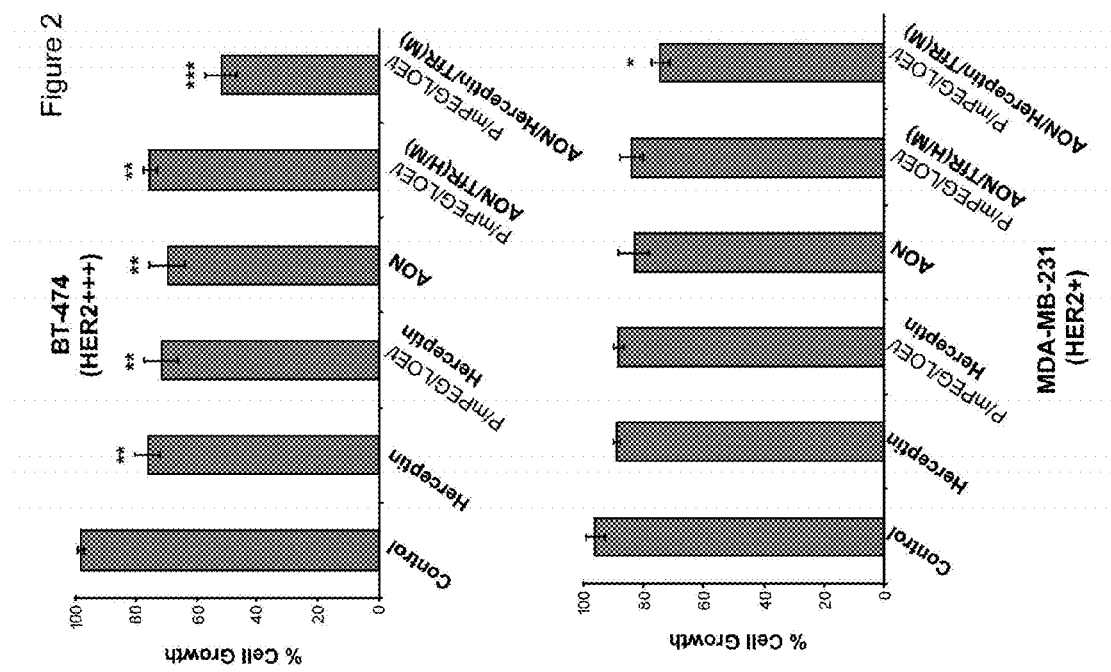

The Lead Nanobiopolymer Carrying Both Herceptin® and HER2/neu AON(P/mPEG/LOEt/AON/Herceptin®/TfR(M)) Inhibited Growth of Breast Cancer Cells In Vitro Breast cancer cell growth inhibition following administration of anti-HER2/neu AON and Herceptin® was first examined. Based on optimization experiments, each of AON at 4 µM with 4 µM Endoporter (in vitro AON delivery agent, GeneTools), and Herceptin®, at 40 µg/ml was analyzed. Results in FIG. 2 are shown for HER2/neu high-expressing cells BT474 and SKBR-3, as well as for low-expressing cells, MDA-MB-231 and MDA-MB-435. Referring to this figure, HER2/neu overexpressing breast cancer cells (BT-474 and SKBR-3; also shown in FIG. 3A) were treated with various drugs as indicated (top row). After 72 hours, cell viability was determined using a Trypan Blue exclusion assay. Percentage of cell growth was calculated as average cell counts for each group and expressed relative to parallel samples treated with PBS (control) set to 100%. Growth of tumor cells treated with lead compound P/mPEG/LOEt/AON/Herceptin®/TfR(M) was observed to be significantly inhibited compared with other treatments in both cell lines. In cell lines expressing low amounts of HER2/neu (FIG. 3A), the data showed that the lead compound had greatest ability to inhibit cell growth (bottom row). One asterisk indicates that $P<0.05$; two asterisks indicate that $P<0.01$; three asterisks indicate that $P<0.003$ compared to PBS control treatment. The lead compound also showed significant differences at $P<0.005$ when compared to all treatment groups (top row), and at $P<0.02$ when compared to Herceptin® (bottom row). At the concentrations used, it was observed that each of free AON and Herceptin® resulted in some growth inhibition in HER2/neu high-expressing cells.

Low-expressing cell lines were observed to be significantly less responsive to these treatments.

These nanobiopolymeric conjugates (a two-drug compound and single-drug compounds shown in FIG. 1) were then tested for tumor cell growth inhibitory effect. The nanobiopolymers, Herceptin®, and free AON caused significant growth inhibition compared to PBS control in HER2/neu high-expressing cells (FIG. 2 top, P<0.01). The lead two-drug compound produced the strongest inhibitory effect that was significantly higher than that of the other nanobiopolymers tested and higher than Herceptin® (P<0.005 compared to all groups). In HER2/neu low-expressing cells, only the lead compound with AON, Herceptin® and TfR(M) was able to induce statistically significant inhibition of tumor growth compared to PBS (FIG. 2 bottom, P<0.02).

Example 15

The Lead Compound Inhibits HER2/Neu and p-Akt Expression and Induces Apoptosis of HER2/neu-Overexpressing Breast Cancer Cells In Vitro A phosphatidylinositol-3 kinase (PI3K) and its downstream target, the serine/threonine kinase Akt, play an important role in HER2/neu positive breast cancer cell growth and proliferation, as well as in anti-tumor effect of Herceptin® (Tseng P H et al, 2006 Mol. Pharmacol. 70:1534; Yakes F M et al. 2002 Cancer Res. 62:4132). HER2/neu signaling can activate the PI3K/Akt/mTOR cascade, and activated Akt stimulates increases in cell size, metabolism and survival (Plas D R et al. 2005 Oncogene 24:7435).

Therefore, to examine the mechanism responsible for the enhanced growth inhibitory effect of the lead nanobiopolymer, drug effects on the expression and phosphorylation of pertinent signaling markers HER2/neu, Akt, and p-Akt were assessed.

HER2/neu high-expressing cell lines BT-474 and SKBR-3 were used (FIG. 3A). To determine whether the nanobiopolymer carrying both HER2/neu AON and Herceptin® induces apoptosis, PARP cleavage was examined by western blot analysis. Breast cancer cell lines used in Examples herein were observed to express high levels of TfR.

In HER2/neu high-expressing cell lines, HER2/neu expression was inhibited to different extents by each of Herceptin®, AON, and the single-drug versions of the nanobiopolymer [P/mPEG/LOEt/Herceptin and P/mPEG/LOEt/AON/TfR(H/M)] in comparison with controls. The strongest inhibition of HER2/neu expression was observed upon treatment with the lead nanobiopolymer having AON and Herceptin® attached to the PMLA carrier molecule.

Expression of p-Akt, a key downstream mediator of HER2/neu signaling (Tseng P H et al, 2006 Mol. Pharmacol. 70:1534), was inhibited to different extents in tumor cells treated with Herceptin®, AON, or single-drug versions of nanobiopolymer compared to control cells treated with PBS or AON transduction reagent Endoporter. The p-Akt signal upon treatment of both breast cancer cell lines with the lead drug carrying both Herceptin® and HER2/neu AON was observed to be markedly lower in comparison to treatment with any other agent (FIG. 3B). The amount of total Akt on western blots remained unchanged by each of the treatment.

Apoptosis assessed by PARP cleavage was induced to some extent by each of Herceptin®, AON, and single-drug nanobiopolymers in HER2/neu high-expressing cells, for example in BT-474 cell line. Significantly, the lead compound, P/mPEG/LOEt/AON/Herceptin®/TfR(M), triggered apoptosis to a greater extent than the other agents in both cell lines, as shown by increased PARP cleavage compared to the other agents (FIG. 3B).

Western blot analyses showed decreased HER2/neu and phosphorylated Akt after treatment with each of Herceptin®, P/mPEG/LOEt/Herceptin®, AON or P/mPEG/LOEt/AON/TfR(H/M)-treated tumor cells, and not with control treatment PBS or Endoporter in both cell lines. Treatment with lead compound P/mPEG/LOEt/AON/Herceptin®/TfR(M) further reduced both HER2/neu and p-Akt. Assay of generation of cleaved poly(ADP-ribose) polymerase (PARP) as a measure of apoptosis was observed at highest levels in P/mPEG/LOEt/AON/Herceptin®/TfR(M)-treated cells. Glyceraldehyde 3-phosphate dehydrogenase (GAPDH) was used as an internal loading control.

Example 16

Figure 4:
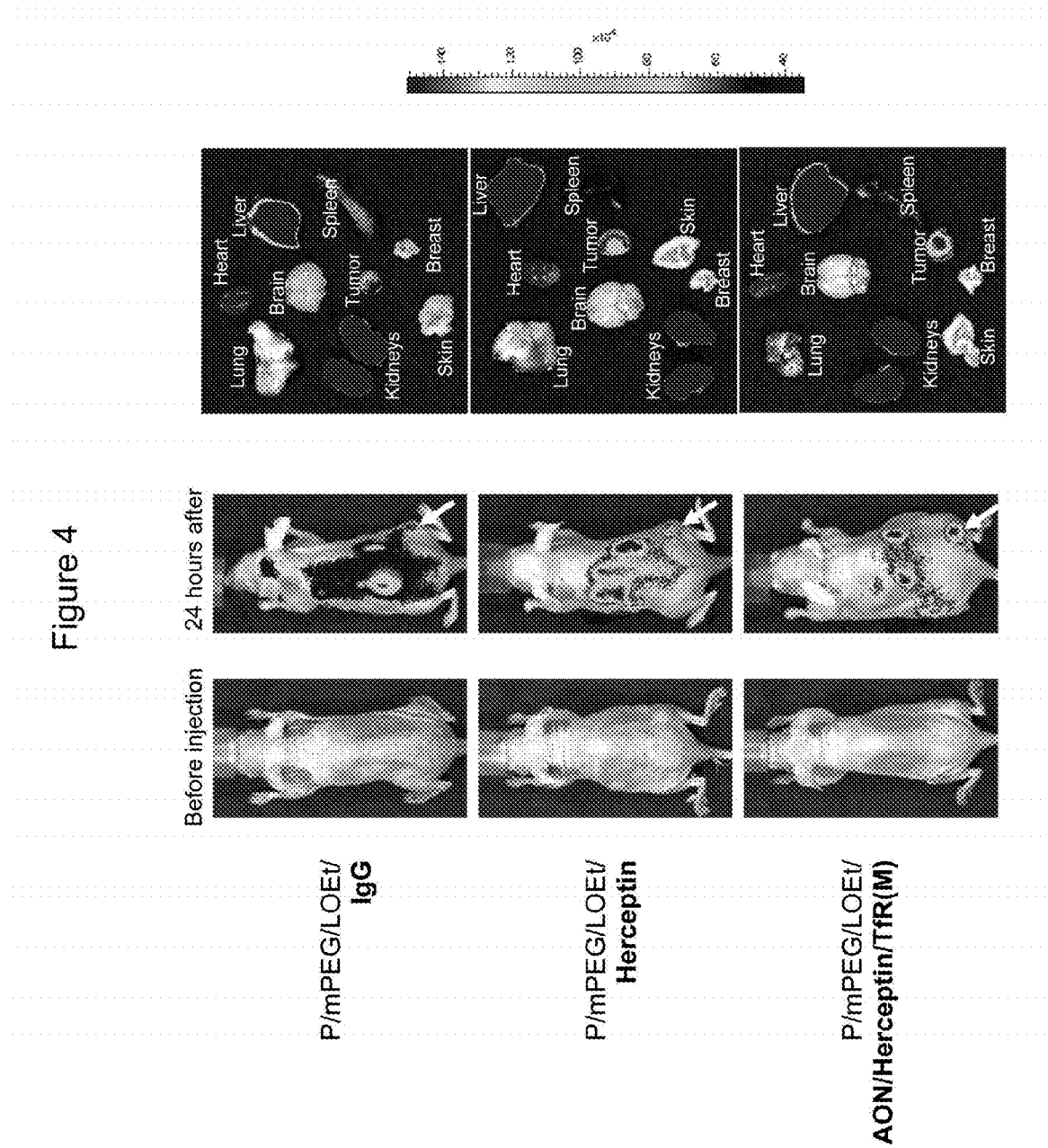
FIG. 4 illustrates distribution of various compounds herein labeled with Alexa Fluor 680 in live mice with BT-474 breast tumors and in tumors in isolated organs.

The Lead Compound P/mPEG/LOEt/AON/Herceptin®/TfR(M) Specifically Accumulates in HER2/Neu-Overexpressing Breast Tumors In Vivo Imaging studies in vivo showed that the lead compound P/mPEG/LOEt/AON/Herceptin®/TfR(M) having anti-mouse TfR and anti-human HER2/neu combined on the same PMLA molecule provided tumor-specific drug delivery through host endothelial system into subcutaneous human breast tumors. Twenty-four hours after injection of drugs, the compounds were observed to accumulate mostly in the tumor and draining organs, kidney and liver (FIG. 4). FIG. 4 shows distribution of various compounds herein labeled with Alexa Fluor 680 in live mice with BT-474 breast tumors and in tumors in isolated organs. Referring to this figure, major organ analysis compared breast tumors and organs before injection (left panel) with those twenty-four hours after intravenous injection (right panels). Live mice herein were injected with each of the lead drug P/mPEG/LOEt/AON/Herceptin®/TfR(M) (bottom row), positive control P/mPEG/LOEt with Herceptin® (middle row) and control conjugate P/mPEG/LOEt/IgG (top row). Control mice (top row) had little BT-474 tumor accumulation, and most of the control polymer accumulated in drug clearing organs, liver and kidneys. Polymer P/mPEG/LOEt with Herceptin® alone had a moderate tumor accumulation (middle row). The highest accumulation in breast tumor cells was observed in mice treated with the lead compound P/mPEG/LOEt/AON/Herceptin®/TfR(M). Arrows mark tumor implantation site.

The nanobiopolymer with only Herceptin® accumulated to a lesser extent in tumors than the version with Herceptin®, AON and anti-TfR mAb (the lead drug). These data show the enhanced targeting of tumor vasculature with anti-TfR mAb compared to Herceptin®. Control nanobiopolymer with IgG showed only a small amount of tumor accumulation (FIG. 4).

Figure 5:
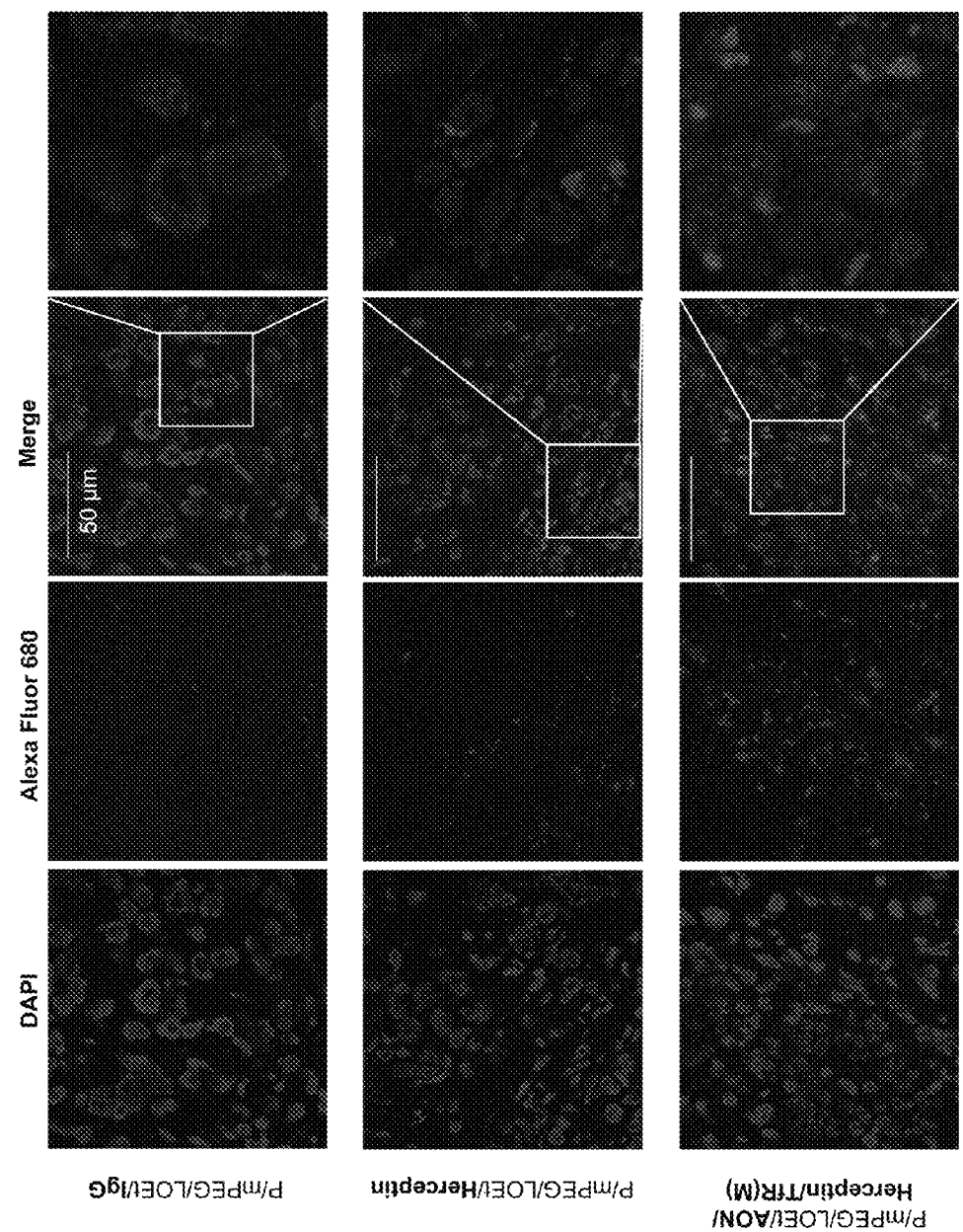
FIG. 5 illustrates distribution of various compounds in BT-474 breast tumor cells.

Confocal microscopy was performed on sections of brain tumors removed 24 hours after intravenous injection of Alexa Fluor 680-labeled drugs. A significantly stronger signal in tumor cells for P/mPEG/LOEt/Herceptin® was observed than for the control conjugate P/mPEG/LOEt/IgG, and the highest tumor accumulation was observed with the lead compound compared to other nanobiopolymers (FIG. 5). FIG. 5 shows distribution of various compounds in BT-474 breast tumor cells. Referring to FIG. 5, animals were administered compounds intravenously as shown in FIG. 4, were sacrificed 24 hours after drug injection, tumors were excised, and sections were analyzed by confocal microscopy. Nuclei were counterstained with DAPI (grey area). Animals injected with control conjugate P/mPEG/LOEt/IgG with attached Alexa Fluor 680 tracking dye (grey) showed little if any tumor cell accumulation (top row). Animals injected with P/mPEG/LOEt/Herceptin® displayed considerable accumulation in tumor cells, and the highest accumulation was observed in animals injected with the lead drug P/mPEG/LOEt/AON/Herceptin®/TfR(M), consistent with live animal imaging data shown in FIG. 4. Scale bar=50 µm.

Example 17

The Lead Compound P/mPEG/LOEt/AON/Herceptin®/TfR(M) Significantly Inhibits HER2/Neu Positive Breast Tumor Growth In Vivo The therapeutic effect of compositions herein following intravenous administration in subcutaneous mouse models of human breast tumor xenografts was investigated. Cell line BT-474 was selected for in vivo analysis because of its high HER2/neu expression and tumorigenicity. Treatment of BT-474 tumor-bearing mice with Herceptin®, single-drug nanobiopolymers and the lead compound P/mPEG/LOEt/AON/Herceptin®/TfR(M) was performed and compared to negative control PBS. No decreases in body weight or morbidity, or death was observed, indicating that each treatment was well tolerated.

Figure 6A:
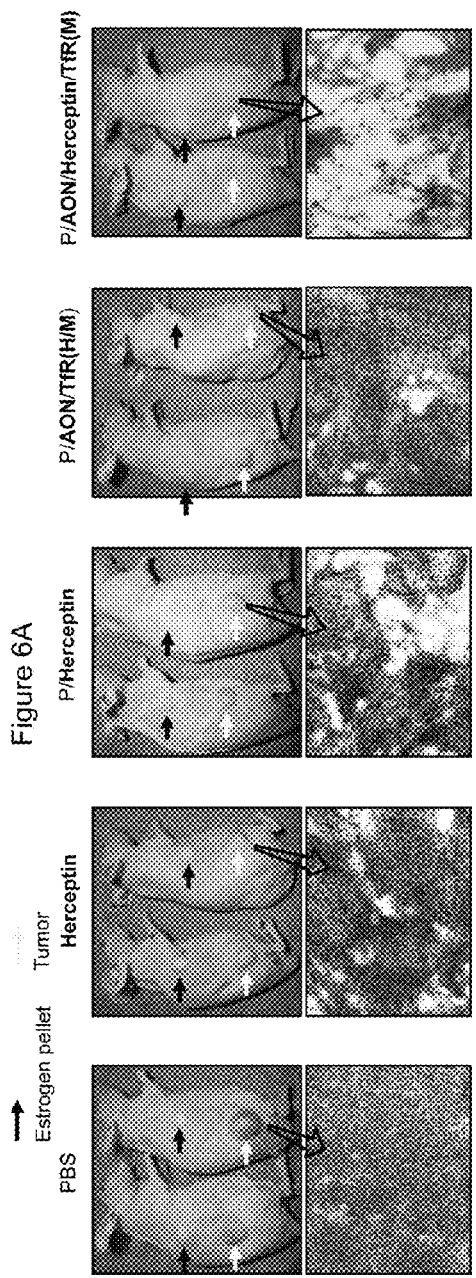
FIGS. 6A-6C illustrate mouse tumor inhibition, pathology, signaling and apoptosis marker expression.
Figure 6C:
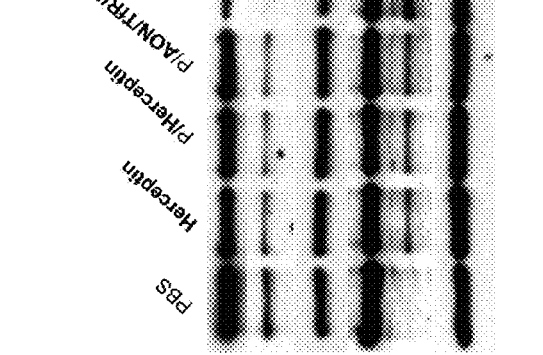
Figure 6B:
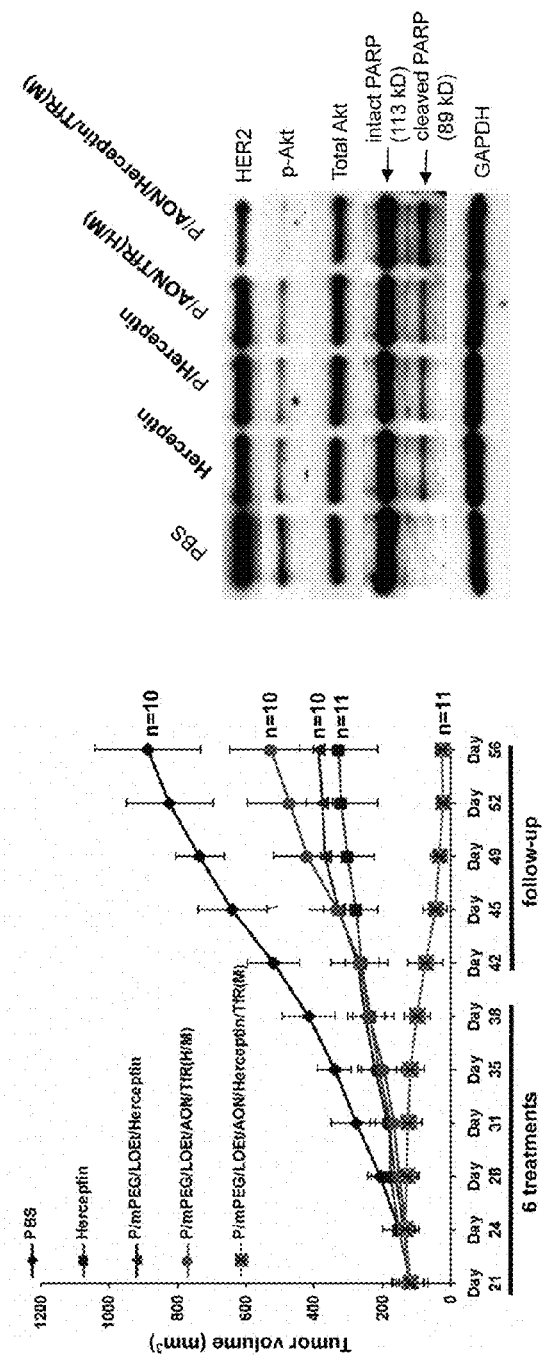

FIGS. 6A-6B show mouse tumor inhibition, pathology, signaling and apoptosis marker expression.

FIG. 6A shows data obtained and histopathological analysis of respective tumors from two representative animals for each group administered with different drugs. Variable amounts of dead tissue were observed to be present in all treated groups. Tumor size reduction data and pronounced disappearance of tumor cells were observed following treatment with the lead drug P/mPEG/LOEt/AON/Herceptin®/TfR(M), and mostly necrotic areas were observed to be present.

FIG. 6B shows extent of tumor growth inhibition in mice. Referring to this figure, animals treated with each of unconjugated Herceptin® (squares) and with positive control P/mPEG/LOEt/Herceptin® (triangles), or with P/mPEG/LOEt/AON/TfR(H/M) (circles) showed significant inhibition compared with PBS control (diamonds) (P<0.03). P/mPEG/LOEt/AON/Herceptin®/TfR(M) treatment (large squares) was observed to produce the greatest inhibition of tumor growth compared to other treatment groups, resulting in 80 to 95% tumor regression observed during the follow-up period (P<0.02 vs. Herceptin® and other drugs; P<0.001 vs. PBS). Error bars denote standard error of the mean (SEM).

FIG. 6C shows expression of select markers after treatment of HER2/neu positive tumors in vivo. Referring to this figure, Western blot analysis data showed a decrease in HER2/neu and p-Akt (but not total Akt) expression in each of Herceptin®-, P/mPEG/LOEt/Herceptin®-, or P/mPEG/LOEt/AON/TfR(H/M)-treated mice and not in control PBS-treated ones. P/mPEG/LOEt/AON/Herceptin®/TfR(M) further inhibited HER2/neu expression, with near disappearance of a p-Akt band. PARP cleavage as a measure of apoptosis was observed also to be substantially greater in P/mPEG/LOEt/AON/Herceptin®/TfR(M)-treated mice than that in other groups. GAPDH was an internal control to normalize gel loading.

Each the compounds inhibited tumor growth after six treatments (from days 21-38 post tumor implantation) and during follow-up to 56 days (FIG. 6B). Control unconjugated Herceptin® showed a similar tumor growth inhibition as a function of time as PMLA-bound Herceptin®. Both these drugs produced a somewhat stronger effect than HER2/neu AON bound to PMLA (FIG. 6B). This effect was significant for all three of these single drug compounds (P<0.03 vs. PBS). The compound having both Herceptin® and HER2/neu AON combined on one nanobiopolymer showed the highest degree of inhibition of tumor growth, with a clear synergistic effect compared to single-drug treatments (FIG. 6B; P<0.001 vs. PBS; P<0.03 vs. other treatment groups). The observed tumor regression following treatment with P/mPEG/LOEt/AON/Herceptin®/TfR(M) was 80% at the start of follow-up to 95% at the end of this period (day 56; FIG. 6B). Moreover, tumors in the group treated with this lead compound started to regress within the two weeks after the initial treatment, and tumors in this group remained suppressed for an additional 20 days, at which time the treatment was terminated.

Hematoxylin and eosin staining revealed that the tumors treated with each of Herceptin®, P/mPEG/LOEt/Herceptin®, or P/mPEG/LOEt/AON/TfR(H/M) showed some areas of cell death compared with PBS (control) treated tumor. Significantly, treatment with the lead compound led to the appearance of massive morphologically necrotic areas with little unaffected tumor tissue remaining (FIG. 6A).

The mechanism of this antitumor effect was further investigated by western blot analysis using lysates of subcutaneous BT-474 breast tumors after different treatments. Tumor HER2/neu expression was partially inhibited by each of Herceptin®, AON, and single-drug versions of the PMLA nanobiopolymer [P/mPEG/LOEt/Herceptin® and P/mPEG/LOEt/AON/TfR(H/M)] in comparison with PBS controls (FIG. 6C). The lead compound P/mPEG/LOEt/AON/Herceptin®/TfR(M) produced the highest inhibition of HER2/neu tumor expression, consistent with the in vitro western blot analysis. Phosphorylated Akt was also reduced after drug treatments. Again, lead drug P/mPEG/LOEt/AON/Herceptin®/TfR(M) resulted in the most pronounced decrease, with little p-Akt signal observed remaining (FIG. 6C). Total Akt remained unchanged upon treatments, as in the in vitro experiments.

Apoptosis assessed by PARP cleavage was induced to some extent by each of the compounds in HER2/neu high-expressing tumors compared to PBS treatment. Significantly, lead P/mPEG/LOEt/AON/Herceptin®/TfR(M) markedly increased PARP cleavage compared to the other treatments indicating that this nanobiopolymer induced apoptosis to a greater extent than the other used drugs (FIG. 6C).

Example 18

Nanobiopolymer Conjugates Significantly Inhibited Triple Negative Breast Cancer Growth In Vivo Potential therapeutic effects of each of the compounds in Table 2 following intravenous administration using subcutaneous mouse models of human triple-negative breast cancer (TNBC) xenografts were investigated. Cell line MDA-MB-468 was selected for in vivo analysis because it lacked expression of estrogen and progesterone, and the HER2 protein in these cells is expressed normally. Treatment of TNBC tumor-bearing mice was performed with a single-drug nanobiopolymer containing AONs specific for α4 and β1 subunits of laminin-411; or with a single-drug nanobiopolymer containing AONs specific for an epidermal growth factor receptor (EGFR) protein; or with a two-drug nanobiopolymer conjugate combing AONs specific for EGFR protein with AONs specific for α4 and β1 subunits of laminin-411, in comparison with negative control PBS using the treatment protocol schedule shown in Table 2.

TABLE 2

Nanobiopolymer drugs and controls for treatment of triple-negative breast cancers.

| Group 1 (n = 6) | Group 2 (n = 6) | Group 3 (n = 6) | Group 4 (n = 6) |
|---|---|---|---|
| PBS | P/PEG(5%)/ LOEt(40%)/ EGFR(2.1%)/ HuTfR(0.12%)/ MsTfR(0.12) IV twice a week | P/PEG(5%)/ LOEt(40%)/ α$_4$β$_1$(2.0%)/ HuTfR(0.12%)/ MsTfR(0.12) IV twice a week | P/PEG(5%)/ LOEt(40%)/ EGFR, α4β$_1$(2.0)/ HuTfR(0.12%)/ MsTfR(0.12) IV twice a week |
| Amount of drug | 12.5 mg/kg (drug) 2.5 mg/kg of each AON | 25 mg/kg (drug) 2.5 mg/kg of each AON | 37.5 mg/kg (drug) 2.5 mg/kg of each AON |

Figure 7:
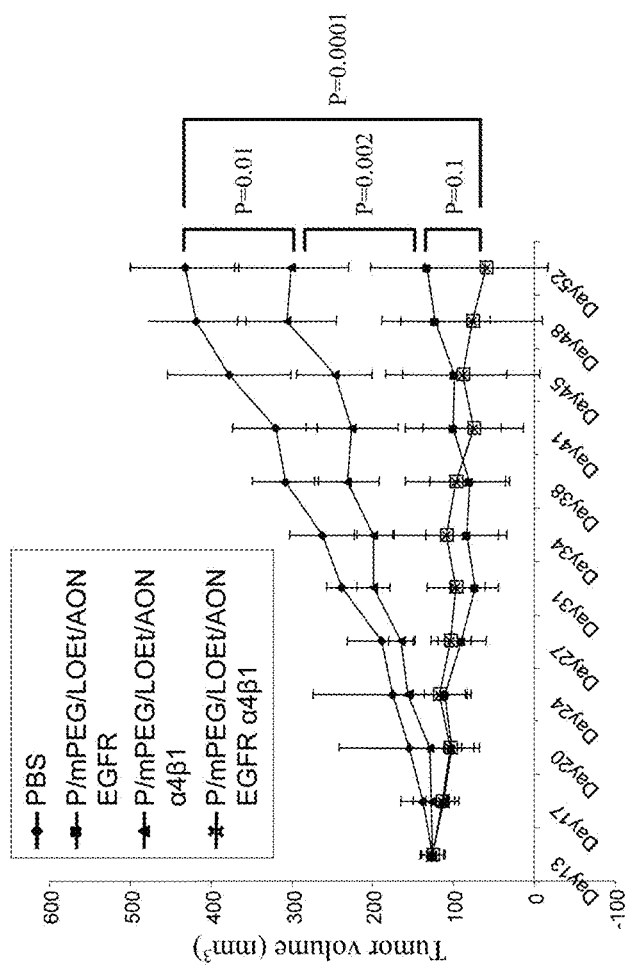
FIG. 7 illustrates extent of tumor growth inhibition by compositions herein in subjects bearing triple-negative breast tumors.

It was observed that single-drug compound carrying AONs specific for EGFR and the two-drug compound carrying both AONs specific for EGFR and AONs specific α4β1-subunits of laminin-411 inhibited tumor growth after six treatments that were administered during days 19-52 after implantation of tumor cells (FIG. 7).

FIG. 7 shows extent of tumor growth inhibition by compositions herein in subjects bearing triple-negative breast tumors. Referring to this figure, animals treated with each of P/mPEG/LOEt/AON-EGFR/TfR(H/M; squares), or with P/mPEG/LOEt/AON-EGFR/α4β1/TfR(H/M; triangles) showed significant inhibition compared with PBS negative control (diamonds). P=0.002 vs. α4β1; P=0.0001 vs. PBS. P/mPEG/LOEt/AON-α4β1/TfR(H/M) treatment inhibited tumor growth compared to control PBS treatment, and was observed to be less effective compared to data obtained with other nanobiopolymers, shown in the figure. (P=0.01 vs. PBS). Error bars denote SEM.

The two-drug compound was observed to have produced a stronger therapeutic effect than the single-drug compound carrying AONs specific for EGFR alone, and the data were statistically significant for each single drug compound and the two-drug compound (P=0.1 vs. PBS). Further, administration on a schedule of the eight treatments was observed to be more effective than six treatments for greater regression of tumors.

Example 19

Nanobiopolymer Conjugates Inhibited Expression of Cancer Stem Cell Markers

Figure 8A:
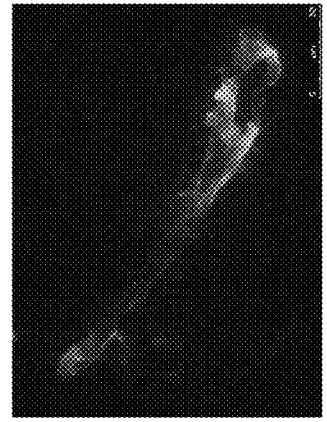
FIGS. 8A-8B illustrate distribution of two cancer stem cell markers, CD44 and c-Myc, in human BT-474 breast tumor cells grown in the brain of nude mice as a model of breast cancer metastasis to the brain, and their inhibition by compositions herein.
Figure 8A:
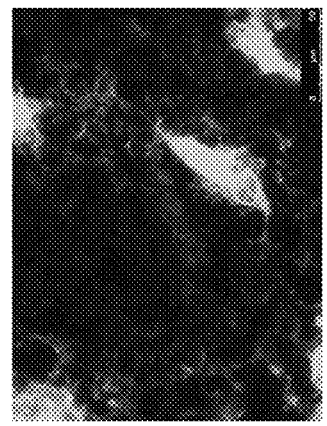
Figure 8B:
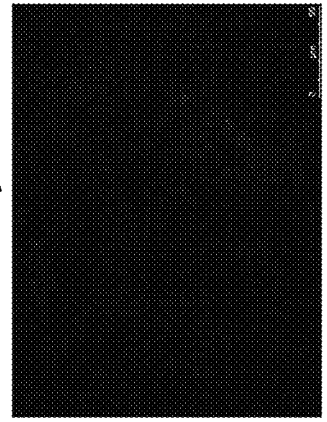
Figure 8B:
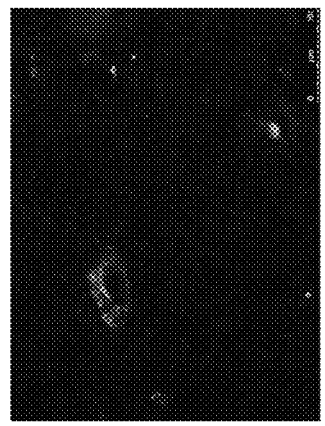

Cancer stem cells represent a population of malignant cells that give rise to the tumor. There are a number of reports describing overexpression of stem cell markers, such as CD133, CD44, Notch1 or C-myc, in human tumors, which coincides with tumor drug resistance (Fan et al. 2004 Cancer Res. 2004; 64:7787-7793; Estrach et al. 2011 Circ Res 109:172-182; Zhang et al. 2008 J Exp Clin Cancer Res 27:85; Wang et al. 2008 PLoS One. 3:e3769; Herschkowitz et al. 2012 Proc Natl Acad Sci USA 109:2778-2783). At the same time, the inhibition of stem cells assessed by marker expression leads to diminishing drug resistance. Therefore, for therapy success it is important to eliminate cancer stem cells expressing markers such as CD133, c-Myc, Nestin, CD44 and Notch1. Using PMLA conjugates to inhibit laminin-411, a number of stem cell markers, such as the ones listed above, were suppressed. FIGS. 8A-8B show distribution of two cancer stem cell markers, CD44 and c-Myc, in human BT-474 breast tumor cells grown in the brain of nude mice as a model of breast cancer metastasis to the brain. Referring to these figures, seven days after tumor inoculation, animals were administered the compounds intravenously as shown in FIG. 4, and treated 6 times over three days with each PBS as a negative control (FIG. 8A) or with P/mPEG/LOEt/AON/Herceptin®/TfR(M) (FIG. 8B). It was observed that immunostaining for both CD44 and c-Myc in tumors treated with P/mPEG/LOEt/AON/Herceptin®/TfR (M) was dramatically reduced compared to tumors treated with control PBS. The expression of cancer stem cell markers was down-regulated after inhibition of synthesis of laminin-411 protein/stem cell marker. Thus, using a nanotechnology approach to treat cancer, such as brain, breast and metastasis from breast and lung cancers, with blockade of laminin-411 with specific cancer targeting, drug resistance may be overcome. Moreover, in HER-2/neu overexpressing primary and metastatic breast tumors, dramatic down-regulation of cancer stem cell markers after multiple intravenous administrations of nanobiopolymer blocking the expression of HER-2 was observed.

Example 20

Advantages of Nanobiopolymers

A set of nanobiopolymeric conjugates specifically tailored for HER2/neu-expressing breast cancer treatment was designed and tested in vitro and in vivo. The drug was based on HER2/neu inhibition by simultaneously blocking the synthesis of HER2/neu with specific AON and internalizing the receptor by binding to Herceptin®. The lead drug P/mPEG/LOEt/AON/Herceptin®/TfR(M) was thus designed to more efficiently inhibit HER2/neu expression and function. In vitro data showed that indeed, the lead drug, P/mPEG/LOEt/AON/Herceptin®/TfR(M), suppressed proliferation of HER2/neu-positive breast cancer cell lines significantly more than Herceptin®, P/mPEG/LOEt/Herceptin® or P/mPEG/LOEt/AON/TfR(H/M) (FIG. 2). Surprisingly, the lead nanobiopolymer was effective for both HER2/neu high- and low-expressing HER2/neu breast cancer cell lines. With regard to HER2/neu low-expressing cells, the lead drug was also superior to previously used HER2/neu AON, which did not inhibit their growth in vitro (Roh H et al. 2000 Cancer Res. 60:560). Moreover, the lead drug carrying both Herceptin® and HER2/neu AON produced the highest inhibition of both HER2/neu expression and Akt phosphorylation, as well as enhanced tumor cell apoptosis, compared to other treatments. Herceptin® mediates antiproliferative effects in HER2/neu-positive cells by facilitating either HER2/neu degradation or endocytic destruction of the HER2/neu receptor or downregulation of PI3K-Akt signaling (Clark A S et al. 2002. Mol Cancer Ther 1:707-17) by inhibiting HER2/neu receptor dimerization, and also by inducing immune activation (Hudis C A 2007 N Engl J Med 357:39).

Examples herein show that the in vitro growth-inhibiting effect of the lead drug carrying both Herceptin® and HER2/ neu AON on tumor cells was enhanced by simultaneous AON-mediated inhibition of HER2/neu synthesis and by downregulation of surface HER2/neu through its binding to Herceptin®. The stronger inhibition of Akt phosphorylation in this case could result from a significant attenuation of HER2/neu signaling.

The lead drug P/mPEG/LOEt/AON/Herceptin®/TfR(M) was observed in examples herein to readily accumulate in breast tumors and dramatically inhibit human breast cancer growth in nude mice (FIG. 6). Importantly, the magnitude of anti-tumor effect of this lead drug indicates synergy between HER2/neu AON and Herceptin® in vivo (FIG. 6). In comparison, the in vitro effect showed about 50% growth inhibition in high HER2/neu-expressing cells, in contrast to nearly complete in vivo inhibition. Without being limited by any particular theory or mechanism of action, the synergistic anti-tumor action in vivo could result from a combination of several effects: enhanced reduction in HER2/neu-mediated tumor growth by AON together with Herceptin®, preferential tumor accumulation mediated by combined EPR effect (Maeda H et al. 2009 Eur J Pharm Biopharm 71:409) and active targeting with antibodies (Ljubimova J Y et al. 2008 Chem Biol Interact 171:195), and maintenance of effective drug concentration due to multiple treatments. Compared to the previously used combination of HER2/neu AON with doxorubicin that was similarly effective against xenogeneic BT-474 tumors (Roh H et al. 2000 Cancer Res. 60:560), the nanobiopolymeric conjugate herein is envisioned as free of side effects because of absence of toxic doxorubicin and of its efficient tumor targeting via Herceptin® and anti-TfR.

Examples herein confirmed that the lead nanobiopolymer P/mPEG/LOEt/AON/Herceptin®/TfR(M) efficiently blocked HER2/neu positive breast tumor growth through dual inhibition of HER2/neu and Akt phosphorylation, and as a result promoted enhanced tumor cell apoptosis. The combination of features of the nanobiopolymer resulted in highly specific drug accumulation in the tumor tissue and inside tumor cells.

Example 21

Nanobiopolymer Platforms for Combinations of Drugs to Treat Breast Cancers

Nanobiopolymer compositions herein can be engineered to include any of at least one of functional modules: an antibody, drug, or AON, alone or in combination. By this characteristic, the nanobiopolymer conjugates herein are nanodrugs that are tailored to target simultaneously different molecular tumor markers typical of particular tumor cells and therefore are highly efficient against various tumors.

For more efficient cancer treatment, nanobiopolymer conjugates of the present invention are covalently linked to one or more antineoplastic agents selected from the following group: a tyrosine kinase inhibitor lapatinib targeting EGFR and HER2 receptor proteins; pertuzumab, a monoclonal antibody (mAb) specific for HER2 receptor; ertumaxomab, a bispecific antibody specific for HER2 and FcγRI/III; trastuzumab-DM1, mAb-toxin specific for HER2; CP-751, 871, mAb specific for IFG-1R; foretinib (GSK136089), a tyrosine kinase inhibitor targeting MET and VEGFRs; BEZ235 targeting proteins of mTOR/PI3K pathway; perifistone targeting Akt pathway; temsirolimus targeting mTOR; everolimus targeting mTOR; HER2 peptide-based vaccines; defucosylated trastuzumab, mAb specific for HER2; dasatinib, a small-molecule tyrosine kinase inhibitor targeting the cytosolic c-SRC and ABL1 kinases, as well as the RTKs c-KIT and platelet-derived growth factor receptors, alpha and beta; and gefitinib and erlotinib, inhibitors of EGFR. It is envisioned that these nanodrugs and nanodrug combinations are effective for treatment of cancer cells in vivo in subjects including human patients.

The nanobiopolymer-based therapy used for treatment of HER2/neu expressing cancer cells and/or triple-negative cancer cells should make a significant clinical impact.

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A drug delivery composition for treating a cancer in a subject comprising:
a plurality of biologically active molecular modules comprising at least one module that targets a tumorigenic cell or a cancer cell, at least one module that inhibits synthesis or activity of a human epidermal growth factor receptor (HER) protein in the tumorigenic cell or the cancer cell, and at least one module for cytoplasmic delivery, wherein the at least one module that targets a tumorigenic cell or a cancer cell includes trastuzumab and an antibody specific for a tumor vasculature protein, and the at least one module that inhibits synthesis or activity of a human epidermal growth factor receptor (HER) protein is a Morpholino AON having a sequence selected from the group consisting of:

```
                                            (SEQ ID NO: 1)
5'-AGGGAGCCGCAGCTTCATGTCTGTG-3',
and (SEQ ID NO: 2)
5'-CATGGTGCTCACTGCGGCTCCGGC-3';
```
and
a polymalic acid-based molecular scaffold, wherein the molecular modules are covalently linked to the scaffold.

2. The drug delivery composition according to claim 1, wherein the vasculature protein comprises a transferrin receptor protein.

3. The drug delivery composition according to claim 1, wherein the antibody is anti-human.

4. The drug delivery composition according to claim 1, wherein the antibody is selected from at least one of: rat anti-mouse, rat anti-human, mouse anti-human, rabbit anti-human and goat anti-human.

5. The drug delivery composition according to claim 1, wherein the at least one module for cytoplasmic delivery comprises an endosome escape unit.

6. The drug delivery composition according to claim 5, wherein the endosome escape unit comprises a leucine ethylester.

7. The drug delivery composition according to claim 1, wherein the plurality of modules further comprises a polyethylene glycol.

8. The drug delivery composition according to claim 1, wherein the polymalic acid-based molecular scaffold comprises a poly(β-L-malic) acid (PMLA).

9. The drug delivery composition according to claim 1 present in a unit dose effective for treatment of the cancer in the subject.

10. The drug delivery composition according to claim 9, wherein the unit dose is at least one selected from the group consisting of: 1 µg/kg, 50 µg/kg, 100 µg/kg, 500 µg/kg, 1 mg/kg, 5 mg/kg, 10 mg/kg, 50 mg/kg, and 100 mg/kg.

11. The drug delivery composition according to claim 1, wherein the cancer is at least one selected from the group consisting of: gastric, endometrial, salivary gland, lung, non-small cell lung, pancreatic, peritoneal, prostate, colorectal, breast, cervical, uterine, ovarian, brain, head and neck, testicular and teratoma cancers.

12. The drug delivery composition according to claim 11, wherein the cancer is selected from the group consisting of a primary cancer and a metastatic cancer.

13. The drug delivery composition according to claim 11, wherein the cancer comprises cells overexpressing a HER2/neu receptor protein.

14. A kit for treating a patient having a cancer comprising a drug delivery composition comprising a nanobiopolymeric conjugate of a scaffold comprising a polymalic acid (PMLA) and molecular modules comprising an antisense molecule that substantially inhibits synthesis or activity of a human epidermal growth factor receptor (HER) protein, wherein the antisense molecule comprises a Morpholino AON having a sequence complementary to a sequence contained in an mRNA transcript of HER2/neu protein, a molecular module to facilitate delivery of the antisense molecule to cytoplasm, at least one targeting antibody specific for the HER2/neu protein, at least one antibody specific for a tumor vasculature protein, and a molecular module that prolongs circulation of the composition, wherein the PMLA is covalently linked to the molecular modules, the at least one targeting antibody comprises trastuzumab and the Morpholino AON comprises a sequence selected from the group consisting of:

```
                                            (SEQ ID NO: 1)
5'-AGGGAGCCGCAGCTTCATGTCTGTG-3',
and (SEQ ID NO: 2)
5'-CATGGTGCTCACTGCGGCTCCGGC-3'.
```

15. The kit according to claim 14 further comprising a pharmaceutically acceptable buffer.

* * * * *